(12) United States Patent
Yagi

(10) Patent No.: US 8,211,551 B2
(45) Date of Patent: Jul. 3, 2012

(54) ORGANIC ELECTROLUMINESCENT DEVICE

(75) Inventor: Kazunari Yagi, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 1083 days.

(21) Appl. No.: 12/122,187

(22) Filed: May 16, 2008

(65) Prior Publication Data

US 2008/0297038 A1 Dec. 4, 2008

(30) Foreign Application Priority Data

May 18, 2007 (JP) ................................. 2007-133111

(51) Int. Cl.
*H01L 51/54* (2006.01)
*C09K 11/06* (2006.01)
(52) U.S. Cl. ........ 428/690; 428/917; 313/504; 313/506; 548/103; 257/E51.044
(58) Field of Classification Search ........................ None
See application file for complete search history.

(56) References Cited

U.S. PATENT DOCUMENTS

| 2001/0019782 A1 | 9/2001 | Igarashi et al. | |
|---|---|---|---|
| 2005/0031903 A1 | 2/2005 | Park et al. | |
| 2007/0128466 A1 * | 6/2007 | Nomura et al. | 428/690 |

FOREIGN PATENT DOCUMENTS

| JP | 2001-247859 A | 9/2001 |
| JP | 2003-109758 A | 4/2003 |
| WO | 2004/085450 A2 | 10/2004 |
| WO | WO 2004/111066 A1 * | 12/2004 |

OTHER PUBLICATIONS

Extended European Search Report dated Sep. 30, 2008, for European App. No. 08009141.6.

* cited by examiner

*Primary Examiner* — Marie R. Yamnitzky
(74) *Attorney, Agent, or Firm* — Sughrue Mion, PLLC

(57) ABSTRACT

An organic electroluminescent device includes a pair of electrodes; and an organic layer between the pair of electrodes, which includes a light-emitting layer and contains a compound represented by the following formula (1):

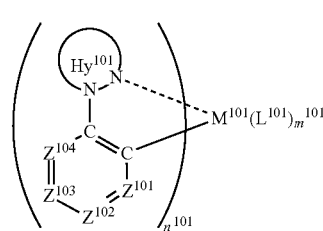

Formula (1)

wherein $M^{101}$ represents a transition metal belonging to group IX of the Periodic Table; $L^{101}$ represents a ligand; $n^{101}$ represents an integer of 1 or more; $m^{101}$ represents an integer of 0 or more; $Hy^{101}$ represents a heterocyclic aromatic ring; $Z^{101}$, $Z^{102}$, $Z^{103}$ and $Z^{104}$ each represents a substituted or unsubstituted carbon atom, or a nitrogen atom; and the dashed line represents a coordinate bond, and the compound represented forms a condensed ring via any of $Z^{101}$ and $Z^{102}$, $Z^{102}$ and $Z^{103}$, and $Z^{103}$ and $Z^{104}$, wherein Z in the crosslinking site forming the condensed ring represents a carbon atom.

7 Claims, 1 Drawing Sheet

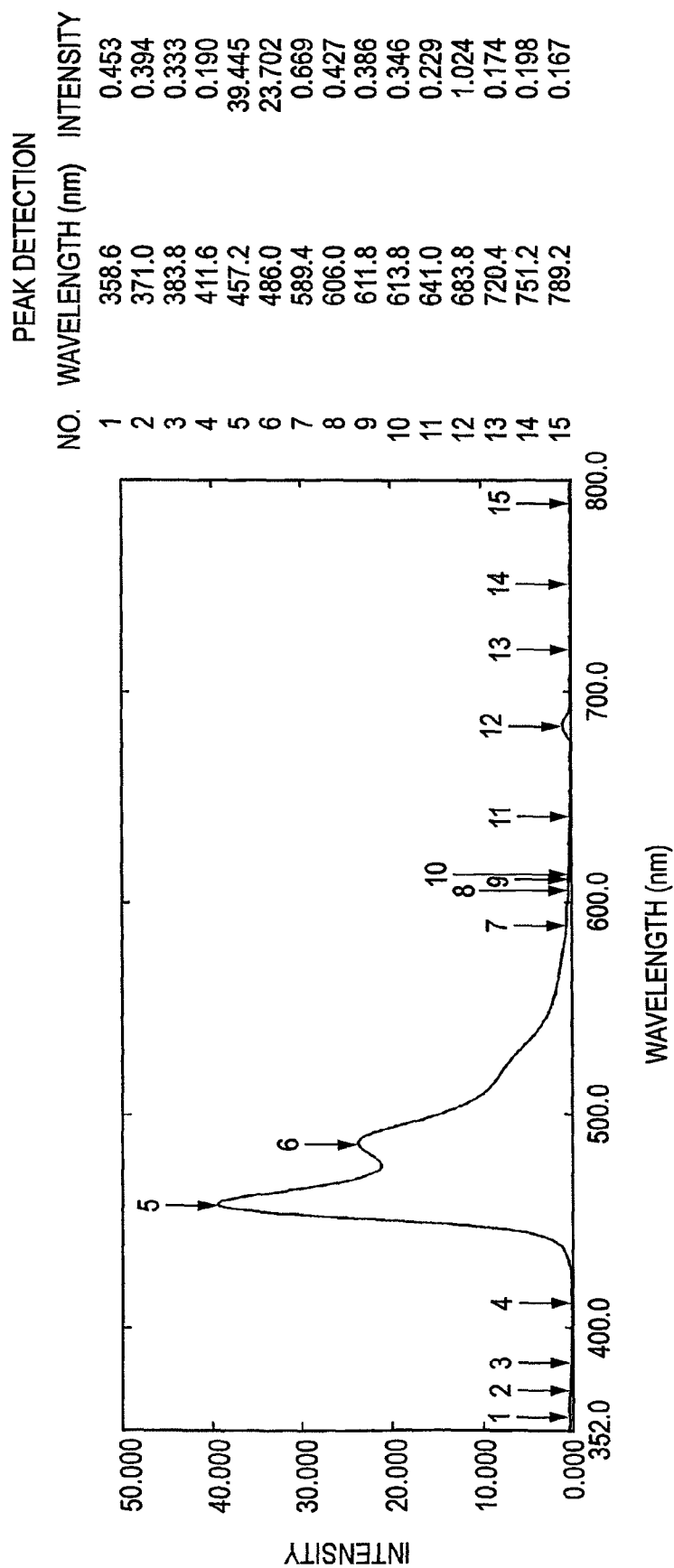

ORGANIC ELECTROLUMINESCENT DEVICE

BACKGROUND OF THE INVENTION

1. Field of the Invention

The present invention relates to a luminescent device capable of emitting light by converting electric energy into light, in particular, relates to an organic electroluminescent device ("luminescent device" or "EL device").

2. Description of the Related Art

Organic electroluminescent devices are attracting public attention as promising display devices for capable of emitting light of high luminance with low voltage. An important characteristic of organic electroluminescent devices is consumed electric power. Consumed electric power is represented by: [Consumed electric power=Voltage×electric current], so that the lower the value of voltage that is necessary to obtain desired brightness and the smaller the value of electric current, the lower is the consumed electric power of the device.

As one trial to lower the value of electric current that flows to a device, a luminescent device utilizing luminescence from ortho-metalated iridium complex (Ir(ppy)$_3$: Tris-Ortho-Metalated Complex of Iridium(III) with 2-Phenylpyridine) is reported (e.g., refer to JP-A-2001-247859 (The term "JP-A" as used herein refers to an "unexamined published Japanese patent application".)). The phosphorescent devices described therein are greatly improved in external quantum efficiency as compared with conventional singlet luminescent devices, and have succeeded in making the value of electric current smaller.

An example to use a phenylpyrazole coordinated iridium complex as a light-emitting material in a blue phosphorescent device is reported (e.g., refer to U.S. 2001/0019782). However, a phenylpyrazole coordinated iridium complex is low in emission quantum efficiency, so that further improvement is desired.

From the viewpoint of the improvement of luminous efficacy of a phenylpyrazole coordinated iridium complex, a biphenylpyrazole coordinated iridium complex is reported (WO 04/085450), but further improvement is required in the points of high luminous efficacy, blue emission of high color purity (maximum luminescent wavelength: 465 nm or less), and long duration of life of devices.

SUMMARY OF THE INVENTION

The invention provides a blue light-emitting material showing good color purity (maximum luminescent wavelength: 465 nm or less). The invention also provides an organic electroluminescent device using the same that satisfies all of high luminous efficacy, long duration of life, and low driving voltage.

The above has been achieved by the following means.

<1> An organic electroluminescent device comprising:

a pair of electrodes; and an organic layer between the pair of electrodes, which comprises a light-emitting layer and contains a compound represented by the following formula (1):

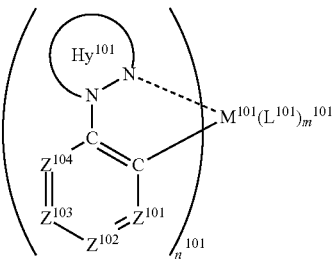

Formula (1)

wherein $M^{101}$ represents a transition metal belonging to group IX of the Periodic Table;

$L^{101}$ represents a ligand;

$n^{101}$ represents an integer of 1 or more;

$M^{101}$ represents an integer of 0 or more;

$Hy^{101}$ represents a heterocyclic aromatic ring;

$Z^{101}$, $Z^{102}$, $Z^{103}$ and $Z^{104}$ each represents a substituted or unsubstituted carbon atom, or a nitrogen atom, and the dashed line represents a coordinate bond, and the compound represented by the formula (1) is bonded to a structure represented by the following formula (2) or (3) via any of $Z^{101}$ and $Z^{102}$, $Z^{102}$ and $Z^{103}$, and $Z^{103}$ and $Z^{104}$ to form a condensed ring, wherein Z in the crosslinking site forming the condensed ring represents a carbon atom:

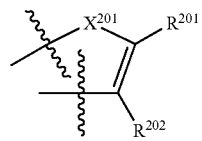

Formula (2)

wherein $X^{201}$ represents an atom belonging to group XVI of the Periodic Table; and $R^{201}$ and $R^{202}$ each represents a hydrogen atom or a substituent, and the structure represented by the formula (2) is bonded to any of $Z^{101}$ and $Z^{102}$, $Z^{102}$ and $Z^{103}$, and $Z^{103}$ and $Z^{104}$ of the formula (1) at the position of the wavy lines:

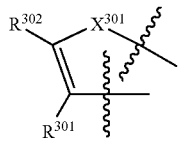

Formula (3)

wherein $X^{301}$ represents an atom belonging to group XVI of the Periodic Table; and $R^{301}$ and $R^{302}$ each represents a hydrogen atom or a substituent, and the structure represented by the formula (3) is bonded to any of $Z^{101}$ and $Z^{102}$, $Z^{102}$ and $Z^{103}$, and $Z^{103}$ and $Z^{104}$ of the formula (1) at the position of the wavy lines.

<2> The organic electroluminescent device of <1>, wherein the compound represented by the formula (1) is a compound represented by the following formula (4):

Formula (4)

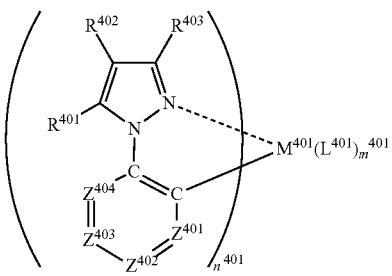

wherein $M^{401}$ represents a transition metal belonging to group IX of the Periodic Table;

$L^{401}$ represents a ligand;

$n^{401}$ represents an integer of 1 or more;

$m^{101}$ represents an integer of 0 or more;

$R^{401}$, $R^{402}$ and $R^{403}$ each represents a hydrogen atom or a substituent;

$Z^{401}$, $Z^{402}$, $Z^{403}$ and $Z^{404}$ each represents a substituted or unsubstituted carbon atom, or a nitrogen atom; and the dashed line represents a coordinate bond, and the compound represented by the formula (4) is bonded to a structure represented by the formula (2) or (3) via any of $Z^{401}$ and $Z^{402}$, $Z^{402}$ and $Z^{403}$, and $Z^{403}$ and $Z^{404}$ to form a condensed ring, wherein Z in the crosslinking site forming the condensed ring represents a carbon atom.

<3> The organic electroluminescent device of <1>, wherein the compound represented by the formula (1) is a compound represented by the following formula (5):

Formula (5)

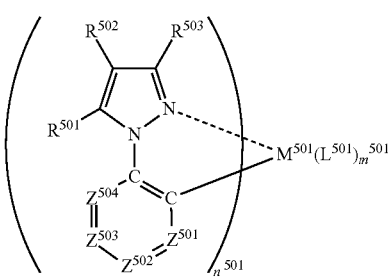

wherein $M^{501}$ represents a transition metal belonging to group LX of the Periodic Table;

$L^{501}$ represents a ligand;

$n^{501}$ represents an integer of 1 or more;

$m^{501}$ represents an integer of 0 or more;

$R^{501}$, $R^{502}$ and $R^{503}$ each represents a hydrogen atom or a substituent;

$Z^{501}$, $Z^{502}$, $Z^{503}$ and $Z^{504}$ each represents a substituted or unsubstituted carbon atom, or a nitrogen atom; and the dashed line represents a coordinate bond, and the compound represented by the formula (5) is bonded to a structure represented by the following formula (6) or (7) via any of $Z^{501}$ and $Z^{502}$, $Z^{502}$ and $Z^{503}$, and $Z^{503}$ and $Z^{504}$ to form a condensed ring, wherein Z in the crosslinking site forming the condensed ring represents a carbon atom:

Formula (6)

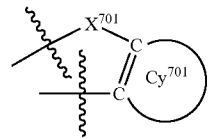

wherein $X^{701}$ represents an atom belonging to group XVI of the Periodic Table; and $Cy^{701}$ represents an aromatic ring or a heterocyclic aromatic ring, and the structure represented by the formula (6) is bonded to any of $Z^{501}$ and $Z^{502}$, $Z^{502}$ and $Z^{503}$, and $Z^{503}$ and $Z^{504}$ of the formula (5) at the position of the wavy lines:

Formula (7)

$$\begin{array}{c} Cy^{801} \\ \end{array} \overset{C}{\underset{C}{\diagup}} \overset{X^{801}}{\diagdown}$$

wherein $X^{801}$ represents an atom belonging to group XVI of the Periodic Table; and $Cy^{801}$ represents an aromatic ring or a heterocyclic aromatic ring, and the structure represented by the formula (7) is bonded to any of $Z^{501}$ and $Z^{502}$, $Z^{502}$ and $Z^{503}$, and $Z^{503}$ and $Z^{504}$ of the formula (5) at the position of the wavy lines.

<4> The organic electroluminescent device of <1>, wherein the compound represented by the formula (1) is a compound represented by the following formula (8):

Formula (8)

$$\left( \begin{array}{c} \text{structure with } R^{601}\text{-}R^{609}, X^{601}, \text{Ir}-(L^{601})_{m601} \end{array} \right)_{n601}$$

wherein $L^{601}$ represents a ligand;

$n^{601}$ represents an integer of 1 or more;

$m^{601}$ represents an integer of 0 or more;

$X^{601}$ represents an oxygen atom or a sulfur atom;

$R^{601}$, $R^{602}$, $R^{603}$, $R^{604}$, $R^{605}$, $R^{606}$, $R^{607}$, $R^{608}$ and $R^{609}$ each represents a hydrogen atom or a substituent; and the dashed line represents a coordinate bond.

<5> The organic electroluminescent device of <1>, wherein the compound represented by the formula (1) is contained in the light-emitting layer.

<6> The organic electroluminescent device of <1>, wherein the light-emitting layer contains a nitrogen-containing organic material as a host material.
<7> The organic electroluminescent device of <1>, wherein the organic layer further comprises an electron-transporting layer containing a metal complex material.
<8> A compound represented by the following formula (8):

Formula (8)

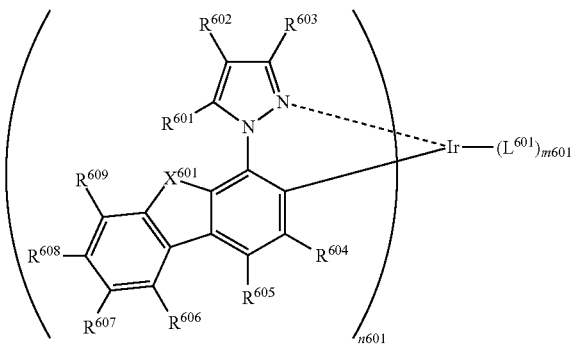

wherein
$L^{601}$ represents a ligand;
$n^{601}$ represents an integer of 1 or more;
$m^{601}$ represents an integer of 0 or more;
$X^{601}$ represents an oxygen atom or a sulfur atom;
$R^{601}, R^{602}, R^{603}, R^{604}, R^{605}, R^{606}, R^{607}, R^{608}$ and $R^{609}$ each represents a hydrogen atom or a substituent; and
the dashed line represents a coordinate bond,

BRIEF DESCRIPTION OF THE DRAWING

FIGURE is the emission spectrum of an iridium complex (Compound 9-1).

DETAILED DESCRIPTION OF THE INVENTION

The compound represented by formula (1) (which is also referred to as a "complex represented by formula (1)" or a "metal complex" hereinafter) will be described below.

Formula (1)

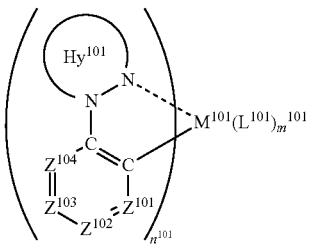

In formula (1), $M^{101}$ represents a transition metal belonging to group IX of the Periodic Table. As $M^{101}$, iridium and rhodium are preferred, and iridium is more preferred. The valence of $M^{101}$ is not especially restricted but monovalent trivalent and tetravalent are preferred, and trivalent is more preferred. The dashed line represents a coordinate bond.
$L^{101}$ represents a ligand (as the bond formed by coordination, there are, e.g., a coordinate bond, a covalent bond and an ionic bond). $L^{101}$ is not especially restricted so long as it represents an atomic group to coordinate to $M^{101}$, but an atomic group to coordinate via a carbon atom, an atomic group to coordinate via a nitrogen atom, an atomic group to coordinate via an oxygen atom, an atomic group to coordinate via a sulfur atom, and an atomic group to coordinate via a phosphorus atom are preferred, an atomic group to coordinate via a carbon atom, an atomic group to coordinate via a nitrogen atom, and an atomic group to coordinate via an oxygen atom are more preferred, and an atomic group to coordinate via a carbon atom and an atomic group to coordinate via a nitrogen atom are still more preferred.

$L^{101}$ may be either a monodentate ligand or a multidentate ligand, but a multidentate ligand is preferred and a bidentate ligand is especially preferred. (A multidentate ligand is a ligand having a plurality of sites to coordinate to metal atoms. It is preferred for a multidentate ligand to contain an atomic group to coordinate via a carbon atom, an atomic group to coordinate via a nitrogen atom, an atomic group to coordinate via an oxygen atom, an atomic group to coordinate via a sulfur atom, and an atomic group to coordinate via a phosphorus atom, it is more preferred to contain an atomic group to coordinate via a carbon atom, an atomic group to coordinate via a nitrogen atom, and an atomic group to coordinate via an oxygen atom, and it is still more preferred to contain an atomic group to coordinate via a carbon atom and an atomic group to coordinate via a nitrogen atom.)

As the atomic group to coordinate via a carbon atom, e.g., an imino ligand, an aromatic hydrocarbocyclic ligand (benzene, naphthalene, etc.), a heterocyclic ligand (thiophene, pyridine, pyrazine, pyrimidine, pyridazine, triazine, thiazole, oxazole, pyrrole, imidazole, pyrazole, triazole, etc.), and condensed rings containing any of these ligands, and tautomers of these ligands are exemplified. These ligands may further have a substituent (it is preferred not to have a substituent). As the examples of the substituents, the groups that will be described later in the substituents on $Hy^{101}$ are exemplified, and the preferred range is also the same.

As the atomic group to coordinate via a nitrogen atom, e.g., a nitrogen-containing heterocyclic ligand (pyridine, pyrazine, pyrimidine, pyridazine, triazine, thiazole, oxazole, pyrrole, imidazole, pyrazole, triazole, etc.), an amino ligand (an alkylamino group (preferably having from 2 to 30 carbon atoms, more preferably from 2 to 20 carbon atoms, and especially preferably from 2 to 10 carbon atoms, e.g., methylamino), an arylamino group (e.g., phenylamino), etc., are exemplified), an acylamino ligand (preferably having from 2 to 30 carbon atoms, more preferably from 2 to 20 carbon atoms, and especially preferably from 2 to 10 carbon atoms, e.g., acetylamino, benzoylamino, etc., are exemplified), an alkoxycarbonylamino group (preferably having from 2 to 30 carbon atoms, more preferably from 2 to 20 carbon atoms, and especially preferably from 2 to 12 carbon atoms, e.g., methoxycarbonyl-amino, etc., are exemplified), an aryloxycarbonylamino group (preferably having from 7 to 30 carbon atoms, more preferably from 7 to 20 carbon atoms, and especially preferably from 7 to 12 carbon atoms, e.g., phenyloxycarbonylamino, etc., are exemplified), a sulfonylamino group (preferably having from 1 to 30 carbon atoms, more preferably from 1 to 20 carbon atoms, and especially preferably from 1 to 12 carbon atoms, e.g., methanesulfonylamino, benzenesulfonylamino, etc., are exemplified), and an imino ligand, etc., are exemplified. These ligands may further be substituted. As the examples of the substituents, the groups that will be described later in the substituents on $Hy^{101}$ are exemplified, and the preferred range is also the same.

As the atomic group to coordinate via an oxygen atom, e.g., an alkoxyl ligand (preferably having from 1 to 30 carbon atoms, more preferably from 1 to 20 carbon atoms, and especially preferably from 1 to 10 carbon atoms, e.g., methoxy, ethoxy, butoxy, 2-ethylhexyloxy, etc., are exemplified), an aryloxy ligand (preferably having from 6 to 30 carbon atoms, more preferably from 6 to 20 carbon atoms, and especially preferably from 6 to 12 carbon atoms, e.g., phenyloxy, 1-naphthyloxy, 2-naphthyloxy, etc., are exemplified), a heterocyclic oxy ligand (preferably having from 1 to 30 carbon atoms, more preferably from 1 to 20 carbon atoms, and especially preferably from 1 to 12 carbon atoms, e.g., pyridyloxy, pyrazyloxy, pyrimidyloxy, quinolyloxy, etc., are exemplified), an acyloxy ligand (preferably having from 2 to 30 carbon atoms, more preferably from 2 to 20 carbon atoms, and especially preferably from 2 to 10 carbon atoms, e.g., acetoxy, benzoyloxy, etc., are exemplified), a silyloxy ligand (preferably having from 3 to 40 carbon atoms, more preferably from 3 to 30 carbon atoms, and especially preferably from 3 to 24 carbon atoms, e.g., trimethylsilyloxy, triphenylsilyloxy, etc., are exemplified), a carbonyl ligand (e.g., a ketone ligand, an ester ligand, an amido ligand, etc.), an ether ligand (e.g., a dialkyl ether ligand, a diaryl ether ligand, a furyl ligand, etc.), etc., are exemplified. These ligands may further be substituted (it is preferred not to have a substituent). As the examples of the substituents, the groups that will be described later in the substituents on $Hy^{101}$ are exemplified, and the preferred range is also the same.

As the atomic group to coordinate via a sulfur atom, e.g., an alkylthio ligand (preferably having from 1 to 30 carbon atoms, more preferably from 1 to 20 carbon atoms, and especially preferably from 1 to 12 carbon atoms, e.g., methylthio, ethylthio, etc., are exemplified), an arylthio ligand (preferably having from 6 to 30 carbon atoms, more preferably from 6 to 20 carbon atoms, and especially preferably from 6 to 12 carbon atoms, e.g., phenylthio, etc., are exemplified), a heterocyclic thio ligand (preferably having from 1 to 30 carbon atoms, more preferably from 1 to 20 carbon atoms, and especially preferably from 1 to 12 carbon atoms, e.g., pyridylthio, 2-benzimidazolylthio, 2-benzoxazolylthio, 2-benzothiazolylthio, etc., are exemplified), a thiocarbonyl ligand (e.g., a thioketone ligand, a thioester ligand, etc.), a thioether ligand (e.g., a dialkyl thioether ligand, a diaryl thioether ligand, a thiofuryl ligand, etc.), etc., are exemplified. These ligands may further be substituted (it is preferred not to have a substituent). As the examples of the substituents, the groups that will be described later in the substituents on $Hy^{101}$ are exemplified, and the preferred range is also the same.

As the atomic group to coordinate via a phosphorus atom, e.g., a dialkylphosphino ligand, a diarylphosphino ligand, a trialkylphosphine ligand, a triarylphosphine ligand, a phosphinine ligand, etc., are exemplified. These ligands may further be substituted (it is preferred not to have a substituent). As the examples of the substituents, the groups that will be described later in the substituents on $Hy^{101}$ are exemplified, and the preferred range is also the same.

$L^{101}$ may further form a polynuclear metal complex by bonding to other metal atom.

$Hy^{101}$ represents a substituted or unsubstituted heterocyclic aromatic ring. As the hetero atoms contained in the heterocyclic aromatic ring, nitrogen, oxygen and sulfur atoms are preferred, and a nitrogen atom is more preferred. As the member of the ring, a 5-membered ring is preferred. $Hy^{101}$ may be a polycyclic aromatic ring. $Hy^{101}$ is preferably unsubstituted.

The examples of the substituents of $Hy^{101}$ include, e.g., an alkyl group (preferably having from 1 to 30 carbon atoms, more preferably from 1 to 20 carbon atoms, and especially preferably from 1 to 10 carbon atoms, e.g., methyl, ethyl, isopropyl, tert-butyl, n-octyl, n-decyl, n-hexadecyl, cyclopropyl, cyclopentyl, cyclohexyl, etc., are exemplified), an alkenyl group (preferably having from 2 to 30 carbon atoms, more preferably from 2 to 20 carbon atoms, and especially preferably from 2 to 10 carbon atoms, e.g., vinyl, allyl, 2-butenyl, 3-pentenyl, etc., are exemplified), an alkynyl group (preferably having from 2 to 30 carbon atoms, more preferably from 2 to 20 carbon atoms, and especially preferably from 2 to 10 carbon atoms, e.g., propargyl, 3-pentynyl, etc., are exemplified), an aryl group (preferably having from 6 to 30 carbon atoms, more preferably from 6 to 20 carbon atoms, and especially preferably from 6 to 12 carbon atoms, e.g., phenyl, p-methylphenyl, naphthyl, anthranyl, etc., are exemplified), an amino group (preferably having from 0 to 30 carbon atoms, more preferably from 0 to 20 carbon atoms, and especially preferably from 0 to 10 carbon atoms, e.g., amino, methylamino, dimethylamino, diethylamino, dibenzylamino, diphenylamino, ditolylamino, etc., are exemplified), an alkoxyl group (preferably having from 1 to 30 carbon atoms, more preferably from 1 to 20 carbon atoms, and especially preferably from 1 to 10 carbon atoms, e.g., methoxy, ethoxy, butoxy, 2-ethylhexyloxy, etc., are exemplified), an aryloxy group (preferably having from 6 to 30 carbon atoms, more preferably from 6 to 20 carbon atoms, and especially preferably from 6 to 12 carbon atoms, e.g., phenyloxy, 1-naphthyloxy, 2-naphthyloxy, etc., are exemplified), a heterocyclic oxy group (preferably having from 1 to 30 carbon atoms, more preferably from 1 to 20 carbon atoms, and especially preferably from 1 to 12 carbon atoms, e.g., pyridyloxy, pyrazyloxy, pyrimidyloxy, quinolyloxy, etc., are exemplified), an acyl group (preferably having from 1 to 30 carbon atoms, more preferably from 1 to 20 carbon atoms, and especially preferably from 1 to 12 carbon atoms, e.g., acetyl, benzoyl, formyl, pivaloyl, etc., are exemplified), an alkoxycarbonyl group (preferably having from 2 to 30 carbon atoms, more preferably from 2 to 20 carbon atoms, and especially preferably from 2 to 12 carbon atoms, e.g., methoxycarbonyl, ethoxycarbonyl, etc., are exemplified), an aryloxycarbonyl group (preferably having from 7 to 30 carbon atoms, more preferably from 7 to 20 carbon atoms, and especially preferably from 7 to 12 carbon atoms, e.g., phenyloxycarbonyl, etc., are exemplified), an acyloxy group (preferably having from 2 to 30 carbon atoms, more preferably from 2 to 20 carbon atoms, and especially preferably from 2 to 10 carbon atoms, e.g., acetoxy, benzoyloxy, etc., are exemplified), an acylamino group (preferably having from 2 to 30 carbon atoms, more preferably from 2 to 20 carbon atoms, and especially preferably from 2 to 10 carbon atoms, e.g., acetylamino, benzoylamino, etc., are exemplified), an alkoxycarbonylamino group (preferably having from 2 to 30 carbon atoms, more preferably from 2 to 20 carbon atoms, and especially preferably from 2 to 12 carbon atoms, e.g., methoxycarbonylamino, etc., are exemplified), an aryloxycarbonylamino group (preferably having from 7 to 30 carbon atoms, more preferably from 7 to 20 carbon atoms, and especially preferably from 7 to 12 carbon atoms, e.g., phenyloxycarbonylamino, etc., are exemplified), a sulfonylamino group (preferably having from 1 to 30 carbon atoms, more preferably from 1 to 20 carbon atoms, and especially preferably from 1 to 12 carbon atoms, e.g., methanesulfonylamino, benzenesulfonylamino, etc., are exemplified), a sulfamoyl group (preferably having from 0 to 30 carbon atoms, more preferably from 0 to 20 carbon atoms, and especially preferably from 0 to 12 carbon atoms, e.g., sulfamoyl, methylsulfamoyl, dimethylsulfamoyl, phenylsulfamoyl, etc., are exemplified), a carbamoyl group (preferably having from 1 to 30 carbon atoms, more preferably from 1 to 20 carbon atoms, and especially preferably from 1 to 12 carbon atoms, e.g., carbamoyl, methylcarbamoyl, diethylcarbamoyl, phenylcarbamoyl, etc., are exemplified), an alkylthio group (preferably having from 1 to 30 carbon atoms, more preferably from 1 to 20 carbon atoms, and especially preferably from 1 to 12 carbon atoms, e.g., methylthio, ethylthio, etc., are exemplified), an arylthio group (preferably having from 6 to 30 carbon atoms, more preferably from 6 to 20 carbon atoms, and especially preferably from 6 to 12 carbon atoms, e.g., phenylthio, etc., are exemplified), a heterocyclic thio group (preferably having from 1 to 30 carbon atoms, more preferably from 1 to 20 carbon atoms, and especially preferably from 1 to 12 carbon atoms, e.g., pyridylthio, 2-benzimizolylthio, 2-benzoxazolylthio, 2-benzo-thiazolylthio, etc., are exemplified), a sulfonyl group (preferably having from 1 to 30 carbon atoms, more preferably from 1 to 20 carbon atoms, and especially preferably from 1 to 12 carbon atoms, e.g., mesyl, tosyl, etc., are exemplified), a sulfinyl group (preferably having from 1 to 30 carbon atoms, more preferably from 1 to 20 carbon atoms, and especially preferably from 1 to 12 carbon atoms, e.g., methanesulfinyl, benzenesulfinyl, etc., are exemplified), a ureido group (preferably having from 1 to 30 carbon atoms, more preferably from 1 to 20 carbon atoms, and especially preferably from 1 to 12 carbon atoms, e.g., ureido, methylureido, phenylureido, etc., are exemplified), a phosphoric acid amido group (preferably having from 1 to 30 carbon atoms, more preferably from 1 to 20 carbon atoms, and especially preferably from 1 to 12 carbon atoms, e.g., diethylphosphoric acid amido, phenylphosphoric acid amido, etc., are exemplified), a hydroxy group, a mercapto group, a halogen atom (e.g., a fluorine atom, a chlorine atom, a bromine atom, an iodine atom), a cyano group, a sulfo group, a carboxyl group, a nitro group, a hydroxamic acid group, a sulfino group, a hydrazino group, an imino group, a heterocyclic group (preferably having from 1 to 30 carbon atoms, and more preferably from 1 to 12 carbon atoms, and as the hetero atoms, e.g., a nitrogen atom, an oxygen atom, a sulfur atom are exemplified, specifically, e.g., imidazolyl, pyridyl quinolyl, furyl, thienyl, piperidyl, morpholino, benzoxazolyl, benzimidazolyl, benzothiazolyl, carbazolyl, azepinyl, etc., are exemplified), a silyl group (preferably having from 3 to 40 carbon atoms, more preferably from 3 to 30 carbon atoms, and especially preferably from 3 to 24 carbon atoms, e.g., trimethylsilyl, triphenylsilyl, etc., are exemplified), a silyloxy group (preferably having from 3 to 40 carbon atoms, more preferably from 3 to 30 carbon atoms, and especially preferably from 3 to 24 carbon atoms, e.g., trimethylsilyloxy, triphenylsilyloxy, etc., are exemplified), and a group having two substituents bonding to each other to form a cyclic structure. When two or more substituents are present, they may be the same or different from each other.

As the preferred range of the substituents on $Hy^{101}$, an alkyl group, an aryl group, an amino group, an alkoxyl group, a halogen atom, a heterocyclic group, and a silyl group are preferred, and a halogen atom, an alkyl group and a silyl group are more preferred, and a halogen atom is especially preferred.

An aromatic ring containing $Z^{101}$, $Z^{102}$, $Z^{103}$ and $Z^{104}$ will be described. $Z^{101}$ to $Z^{104}$ represent a substituted or unsubstituted carbon atom, or a nitrogen atom. Of $Z^{101}$ to $Z^{104}$, a nitrogen atom to be contained is preferably 0 or 1, and more preferably 0. The compound is bonded to the structure represented by formula (2) or (3) via any of $Z^{101}$ and $Z^{102}$, $Z^{102}$ and $Z^{103}$, and $Z^{103}$ and $Z^{104}$ to form a condensed ring (Z in the crosslinking site forming the condensed ring is a carbon atom, for example, when $Z^{101}$ and $Z^{102}$ form a condensed ring, $Z^{101}$ and $Z^{102}$ both represent carbon atoms). It is preferred to form a condensed ring by $Z^{101}$ and $Z^{102}$ part or $Z^{102}$ and $Z^{103}$ part, and it is more preferred to form by $Z^{101}$ and $Z^{102}$ part.

$n^{101}$ represents an integer of 1 or more, preferably an integer of from 1 to 3, more preferably 2 or 3, and especially preferably represents 3. $m^{101}$ represents an integer of 0 or more, preferably an integer of from 0 to 2, more preferably 0 or 1, and especially preferably represents 0.

It is preferred to combine $n^{101}$ and $m^{101}$ so that the complex represented by formula (1) becomes a neutral complex.

The structures represented by formulae (2) and (3) will be described below.

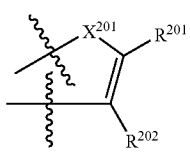

Formula (2)

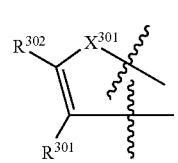

Formula (3)

In formulae (2) and (3), $X^{201}$ and $X^{301}$ each represents an atom belonging to group XVI. $X^{201}$ and $X^{301}$ each preferably represents an oxygen atom or a sulfur atom, and especially preferably an oxygen atom.

$R^{201}$, $R^{202}$, $R^{301}$ and $R^{302}$ each represents a hydrogen atom or a substituent. The substituents here have the same meaning as the substituents defined in the substituents on $Hy^{101}$. It is preferred that $R^{201}$ and $R^{202}$, and $R^{301}$ and $R^{302}$ are bonded to each other to form a cyclic structure (preferably an aromatic ring, and more preferably a monocyclic aromatic ring).

The structures of formulae (2) and (3) are bonded to any of $Z^{101}$ and $Z^{102}$, $Z^{102}$ and $Z^{103}$, and $Z^{103}$ and $Z^{104}$ of formula (1) at the position of the wavy lines.

The compounds represented by formula (4) will be described below.

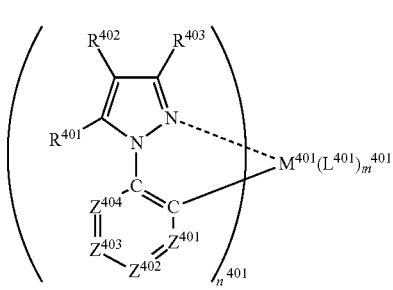

Formula (4)

In formula (4), $M^{401}$ has the same meaning as that described in $M^{101}$, and the preferred range is also the same.

$L^{401}$ represents a ligand and has the same meaning as that described in $L^{101}$, and the preferred range is also the same.

$R^{401}$, $R^{402}$ and $R^{403}$ each represents a hydrogen atom or a substituent. $R^{401}$ to $R^{403}$ each preferably represents a hydrogen atom. The substituents represented by $R^{401}$ to $R^{403}$ have the same meaning as the substituents on $Hy^{101}$ defined above, and the preferred range is also the same.

An aromatic ring containing $Z^{401}$, $Z^{402}$, $Z^{403}$ and $Z^{404}$ will be described. $Z^{401}$ to $Z^{404}$ represent a substituted or unsubstituted carbon atom, or a nitrogen atom. Of $Z^{401}$ to $Z^{404}$, a nitrogen atom to be contained is preferably 0 or 1, and more preferably 0. The compound is bonded to the structure represented by formula (2) or (3) via any of $Z^{401}$ and $Z^{402}$, $Z^{402}$ and $Z^{403}$, and $Z^{403}$ and $Z^{404}$ to form a condensed ring (Z in the crosslinking site forming the condensed ring is a carbon atom, for example, when $Z^{401}$ and $Z^{402}$ form a condensed ring, $Z^{401}$ and $Z^{402}$ both represent carbon atoms). It is preferred to form a condensed ring by $Z^{401}$ and $Z^{402}$ part or $Z^{402}$ and $Z^{403}$ part, and it is more preferred to form by $Z^{401}$ and $Z^{402}$ part. A structure to be bonded is preferably formula (3).

$n^{401}$ represents an integer of 1 or more, preferably an integer of from 1 to 3, more preferably 2 or 3, and especially preferably represents 3.

$m^{401}$ represents an integer of 0 or more, preferably an integer of from 0 to 2, more preferably 0 or 1, and especially preferably represents 0.

It is preferred to combine $n^{401}$ and $m^{401}$ so that the complex represented by formula (4) becomes a neutral complex.

The compound represented by formula (5) will be described below.

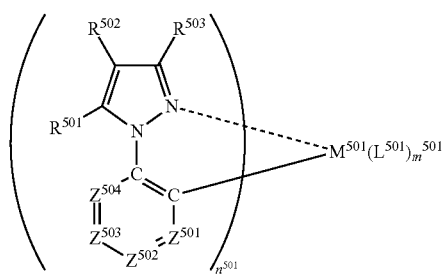

Formula (5)

In formula (5), $M^{501}$ has the same meaning as that described in $M^{101}$, and the preferred range is also the same.

$L^{501}$ represents a ligand and has the same meaning as that described in $L^{101}$, and the preferred range is also the same.

$R^{501}$, $R^{502}$, $R^{503}$ and $R^{504}$ each represents a hydrogen atom or a substituent. $R^{501}$ to $R^{504}$ each preferably represents a hydrogen atom. The substituents represented by $R^{501}$ to $R^{504}$ have the same meaning as the substituents on $Hy^{101}$ defined above, and the preferred range is also the same.

An aromatic ring containing $Z^{501}$, $Z^{502}$, $Z^{503}$ and $Z^{504}$ will be described. $Z^{501}$ to $Z^{504}$ represent a substituted or unsubstituted carbon atom, or a nitrogen atom. Of $Z^{501}$ to $Z^{504}$, a nitrogen atom to be contained is preferably 0 or 1, and more preferably 0. The compound is bonded to a structure represented by formula (6) or (7) (preferably the structure represented by formula (7)) via any of $Z^{501}$ and $Z^{502}$, $Z^{502}$ and $Z^{503}$, and $Z^{503}$ and $Z^{504}$ to form a condensed ring (Z in the crosslinking site forming the condensed ring is a carbon atom, for example, when $Z^{501}$ and $Z^{502}$ form a condensed ring, $Z^{501}$ and $Z^{502}$ both represent carbon atoms). It is preferred to form a condensed ring by $Z^{501}$ and $Z^{502}$ part or $Z^{502}$ and $Z^{503}$ part, and it is more preferred to form by $Z^{501}$ and $Z^{502}$ part.

$n^{501}$ represents an integer of 1 or more, preferably an integer of from 1 to 3, more preferably 2 or 3, and especially preferably represents 3.

$m^{501}$ represents an integer of 0 or more, preferably an integer of from 0 to 2, more preferably 0 or 1, and especially preferably represents 0.

It is preferred to combine $n^{501}$ and $m^{501}$ so that the complex represented by formula (5) becomes a neutral complex.

The structures represented by formulae (6) and (7) will be described below.

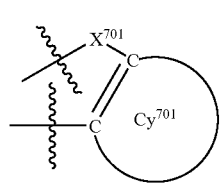

Formula (6)

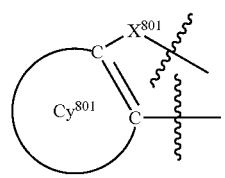

Formula (7)

In formulae (6) and (7), $X^{701}$ and $X^{801}$ each represents an atom belonging to group XVI. $X^{701}$ and $X^{801}$ each preferably represents an oxygen atom or a sulfur atom, and especially preferably an oxygen atom.

$Cy^{701}$ and $Cy^{801}$ each represents an aromatic ring or a heterocyclic aromatic ring. $Cy^{701}$ and $Cy^{801}$ may be a polycyclic aromatic ring, but preferably a monocyclic ring. The number of constituting carbon atoms is preferably from 1 to 20, more preferably from 2 to 10, and especially preferably 6. When $Cy^{701}$ and $Cy^{801}$ each represents a heterocyclic aromatic ring, nitrogen, phosphorus, boron, silicon, oxygen and sulfur are exemplified as the hetero atoms to be contained, nitrogen, sulfur and oxygen are preferred of these, and nitrogen is especially preferred. $Cy^{701}$ and $Cy^{801}$ may have substituents. The substituents here have the same meaning as the substituents on $Hy^{101}$ defined above, and the preferred range is also the same.

The structures represented by formula (6) and (7) are bonded to any of $Z^{501}$ and $Z^{502}$, $Z^{502}$ and $Z^{503}$, and $Z^{503}$ and $Z^{504}$ of formula (5) at the position of the wavy lines The compound represented by formula (8) will be described.

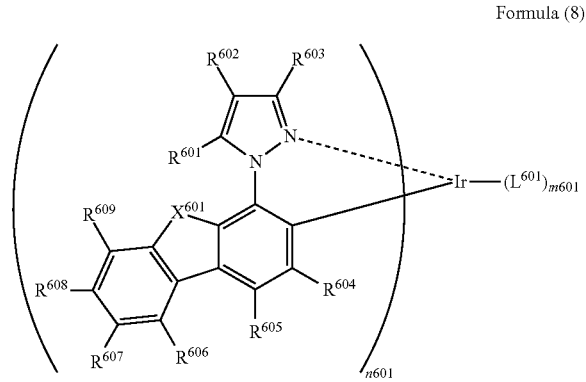

Formula (8)

The valence of iridium is not especially restricted but monovalent, trivalent and tetravalent are preferred, and trivalent is especially preferred.

$L^{601}$ represents a ligand and has the same meaning as that described in $L^{101}$, and the preferred range is also the same.

$n^{601}$ represents an integer of 1 or more, preferably an integer of from 1 to 3, more preferably 2 or 3, and especially preferably represents 3.

$m^{601}$ represents an integer of 0 or more, preferably an integer of from 0 to 2, more preferably 0 or 1, and especially preferably represents 0.

It is preferred to combine $n^{601}$ and $m^{601}$ so that the complex represented by formula (8) becomes a neutral complex.

$X^{601}$ represents an atom belonging to group XVI. $X^{601}$ preferably represents an oxygen atom or a sulfur atom, and especially preferably represents an oxygen atom.

$R^{601}$ to $R^{609}$ each represents a hydrogen atom or a substituent. $R^{601}$ to $R^{609}$ each preferably represents a hydrogen atom. The substituents represented by $R^{601}$ to $R^{609}$ have the same meaning as the substituents on $Hy^{101}$ defined above, and the preferred range is also the same.

The compounds represented by formula (1), (4), (5) or (8) according to the invention can be synthesized by various known methods (e.g., the method disclosed in JP-A-2005-53912). Other compounds can also be synthesized according to known methods.

For example the compound represented by formula (8) can be synthesized according to the same method as the synthesizing method of Compound 9-1 described in EXAMPLE later.

The specific examples of the compounds represented by formula (1), (4), (5) or (8) are shown below, but the invention is not restricted thereto.

9-1

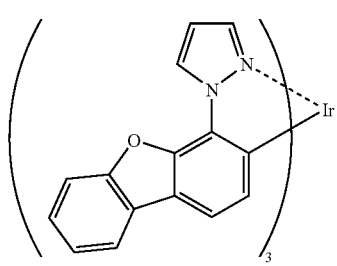

9-2

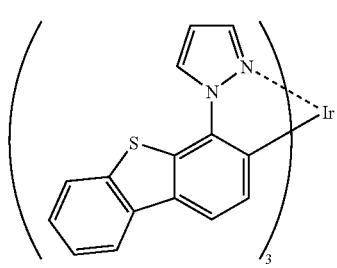

9-3

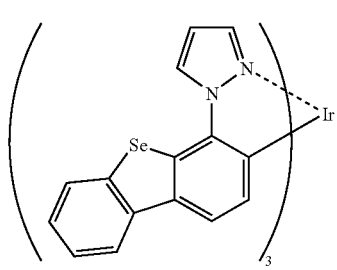

9-4

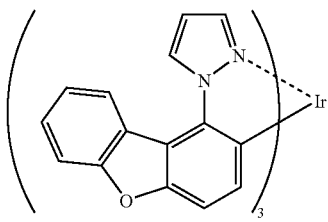

9-5

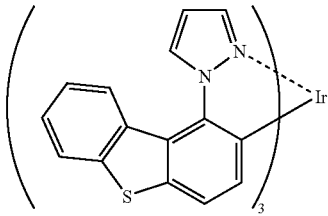

9-6

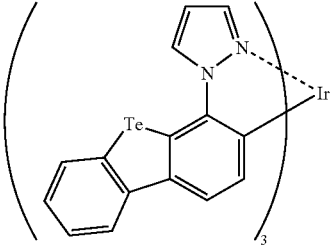

9-7

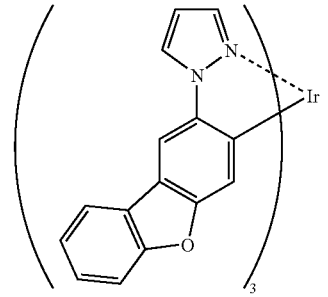

9-8

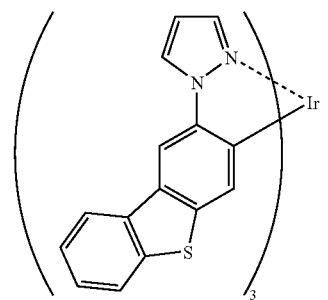

9-9
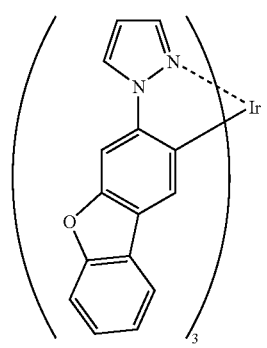
9-10
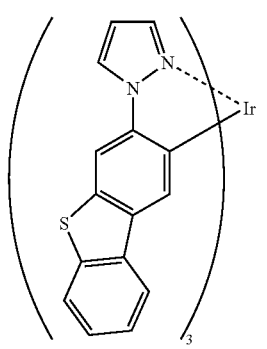
9-11
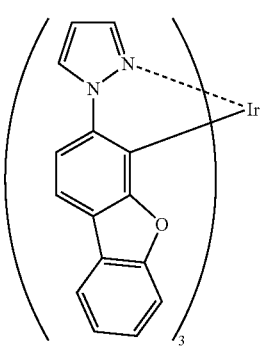
9-12
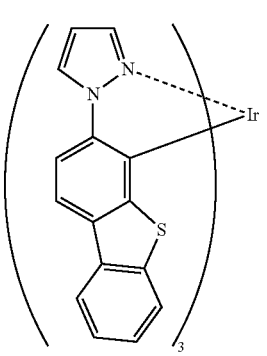
9-13
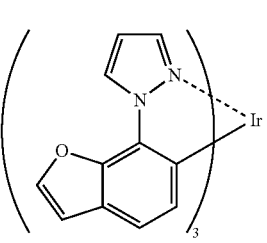
9-14
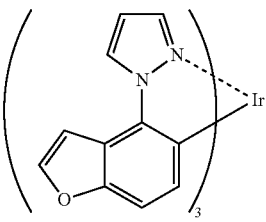
10-1
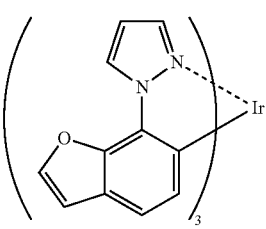
10-2
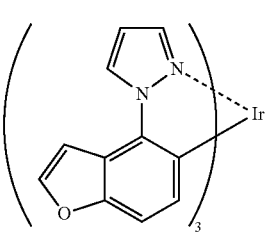
10-3
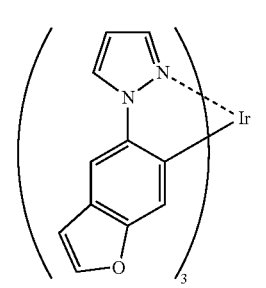
10-4
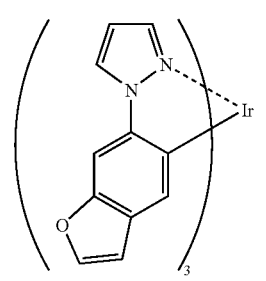
10-5
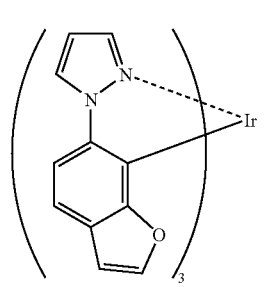

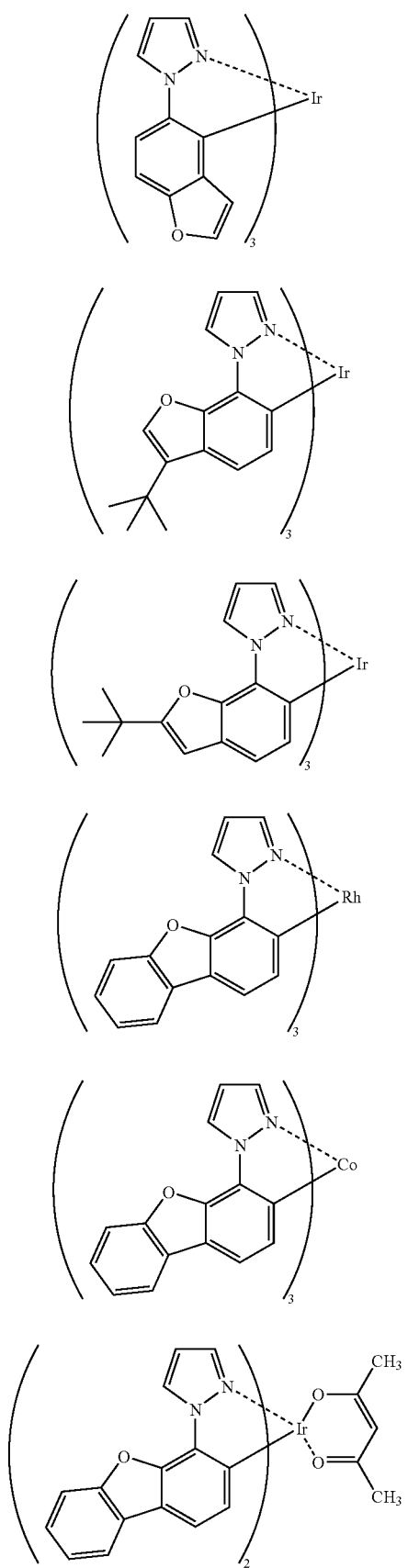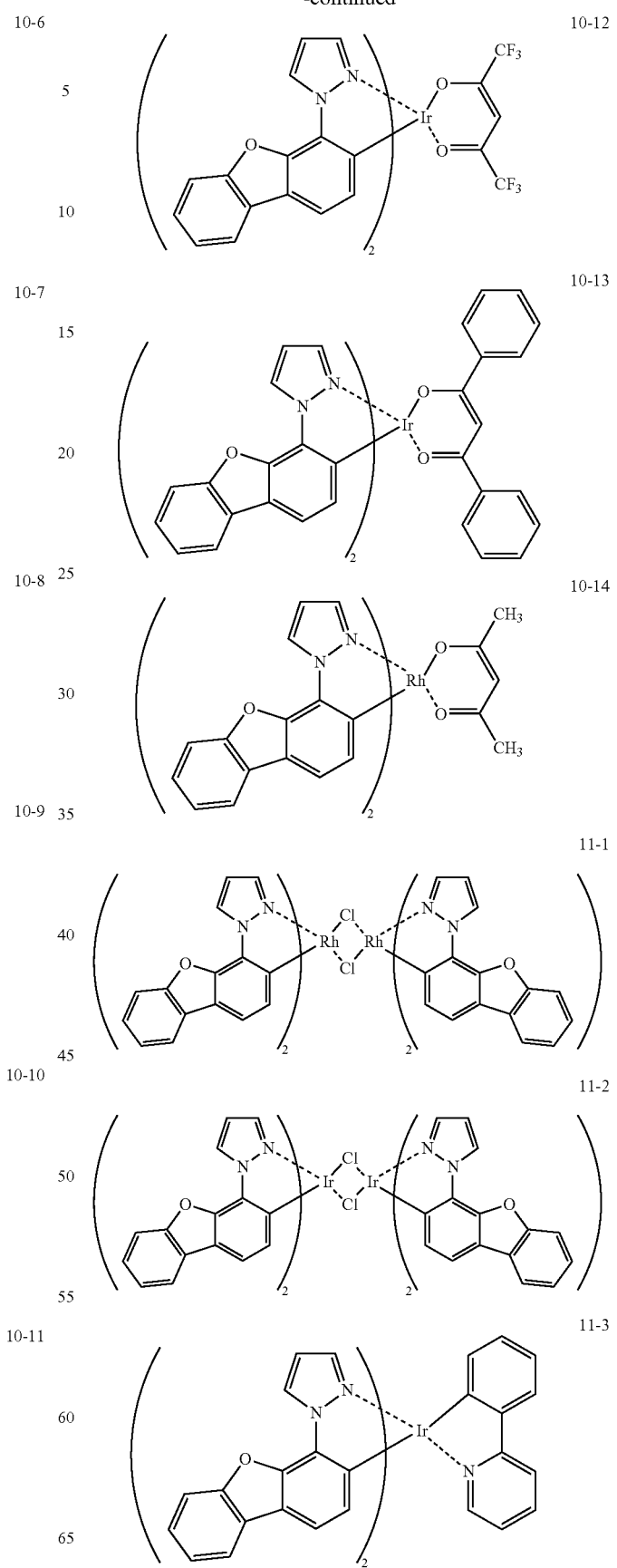

11-4
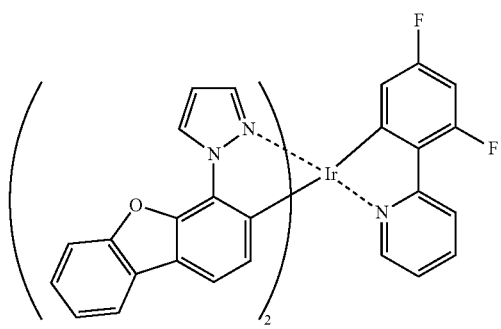
11-5
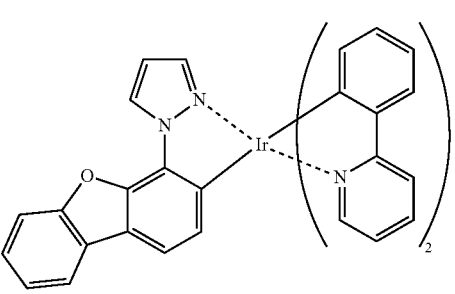
11-6
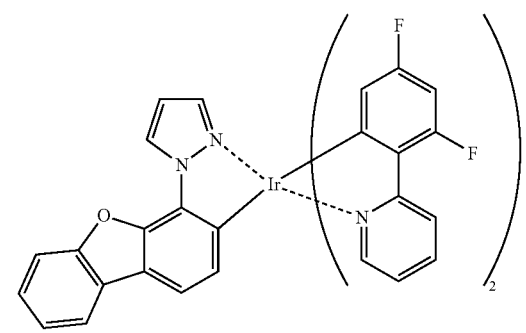
11-7
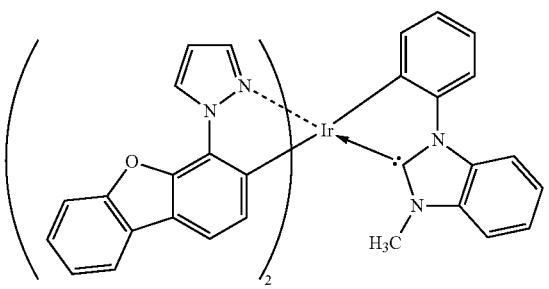
11-8
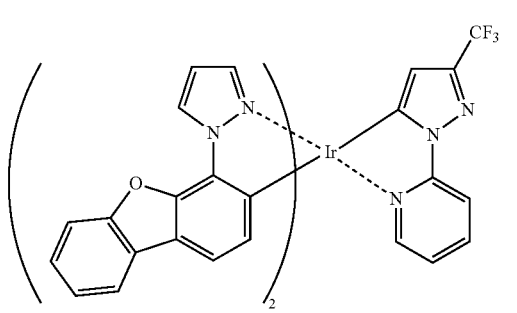
12-1
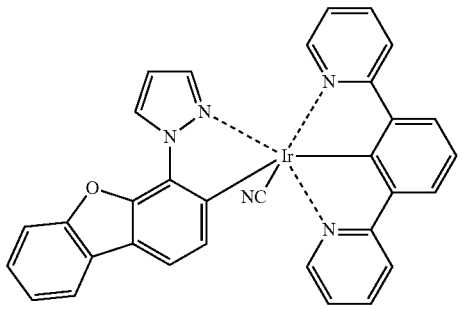
12-2
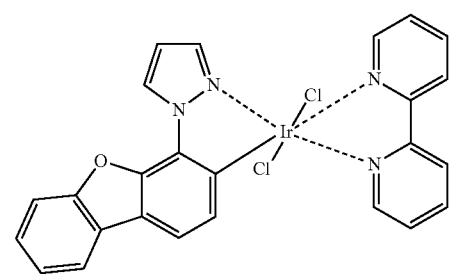
12-3
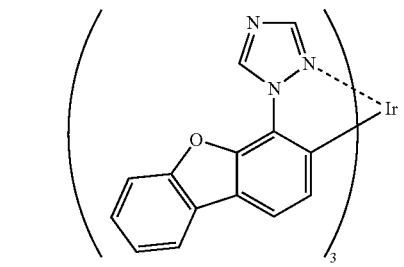
12-4
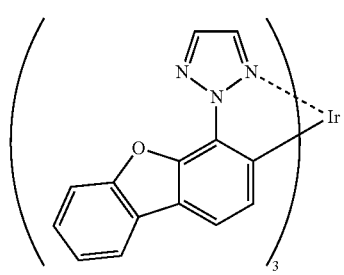
12-5
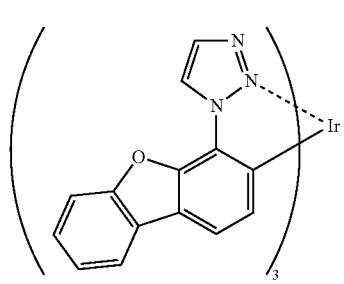

12-6
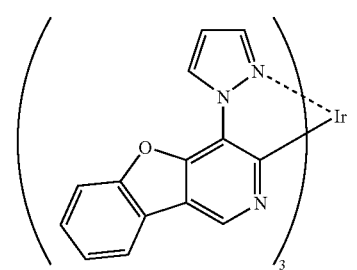
12-7
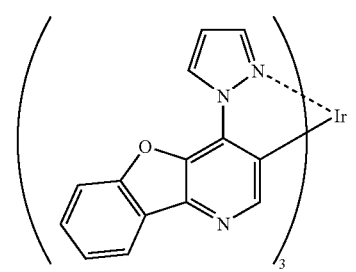
12-8
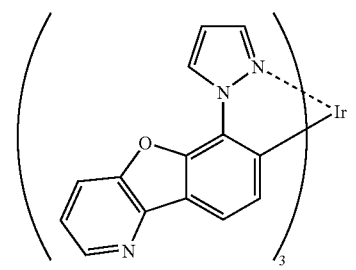
12-9
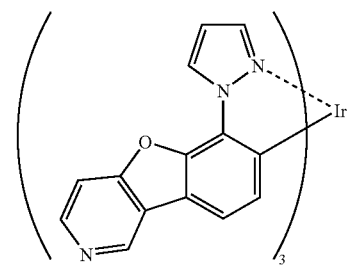
12-10
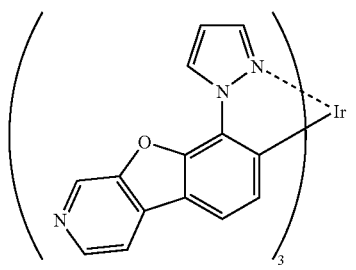
12-11
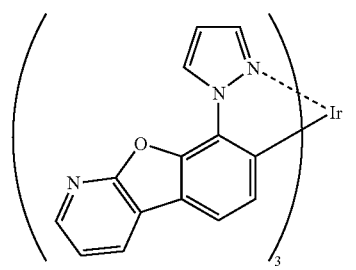
12-12
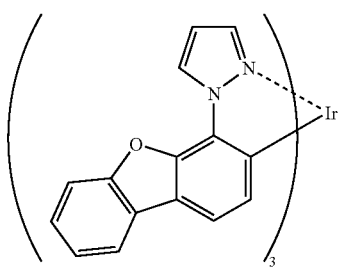
13-1
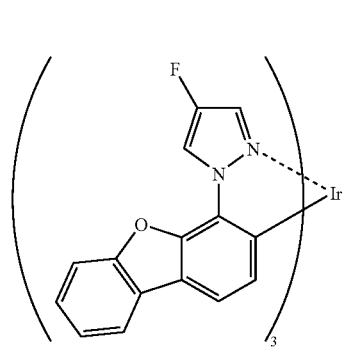
13-2
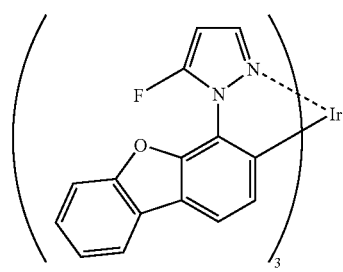
13-3
13-4
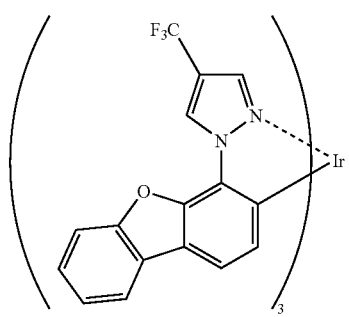

13-5
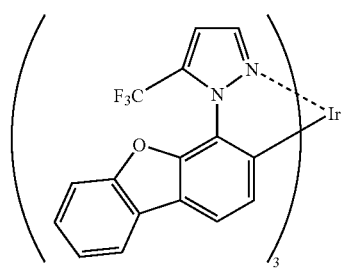
13-6
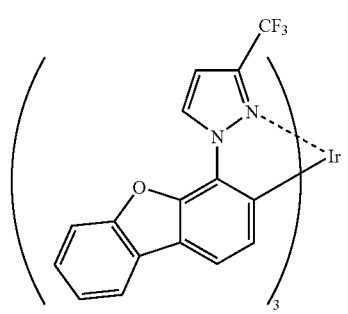
13-7
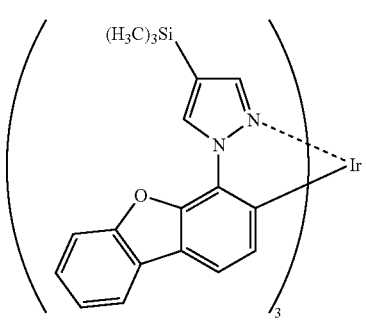
13-8
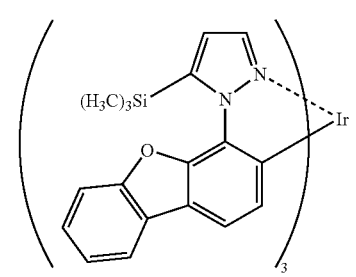
13-9
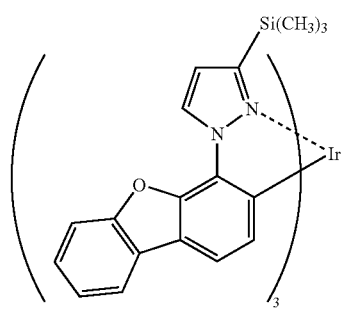
13-10
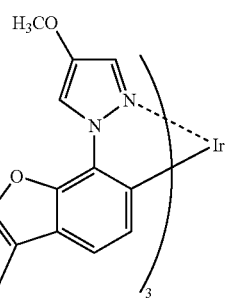
13-11
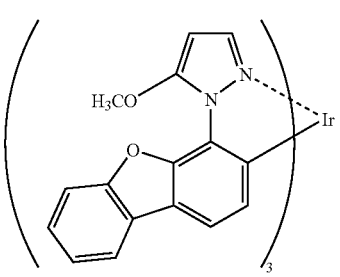
13-12
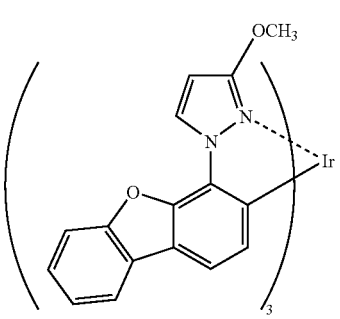
13-13
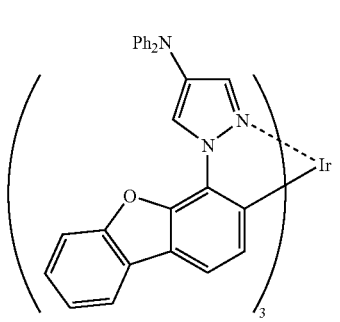
13-14
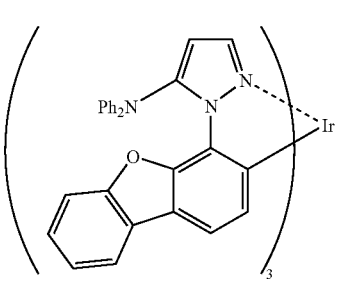

13-15
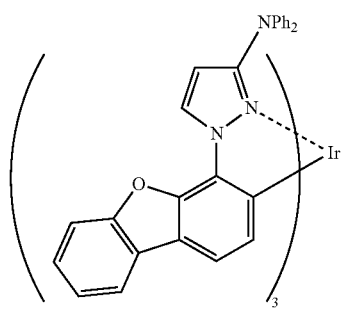
14-1
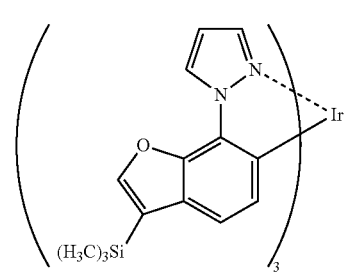
14-2
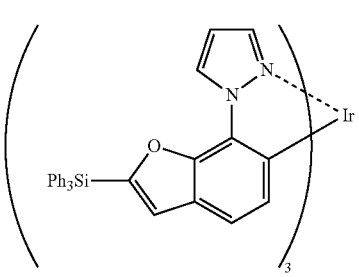
14-3
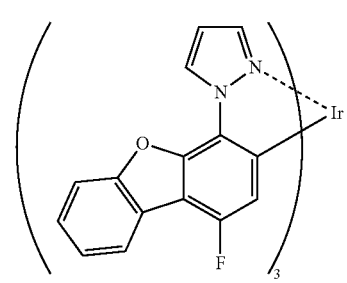
14-4
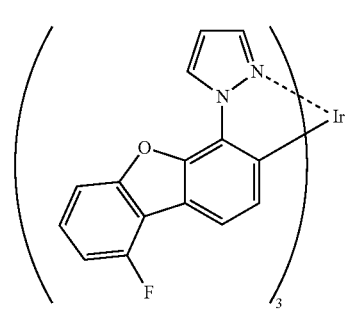
14-5
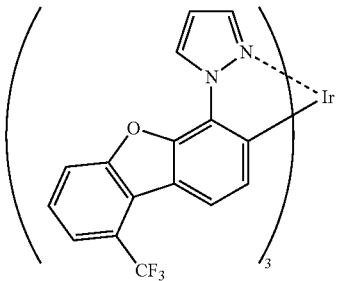
14-6
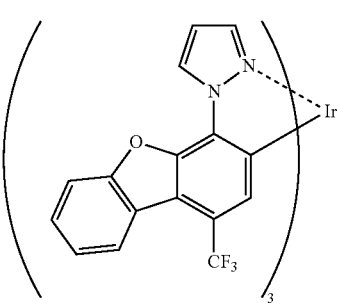
14-7
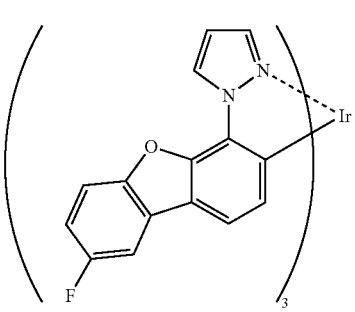
14-8
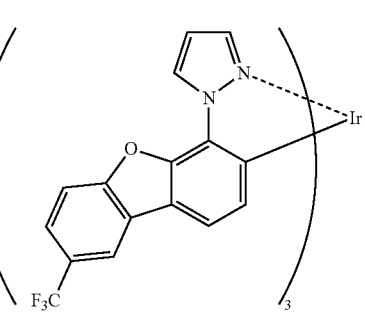
14-9
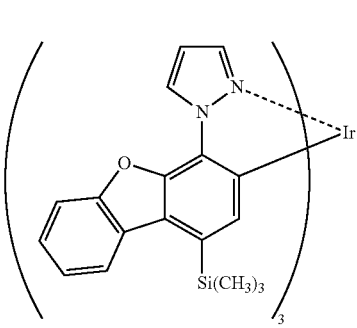

14-10 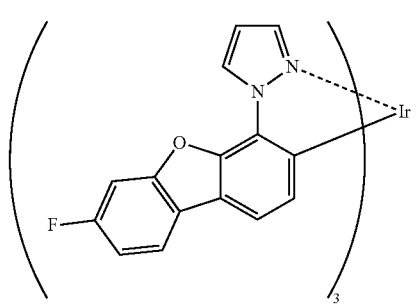
14-11 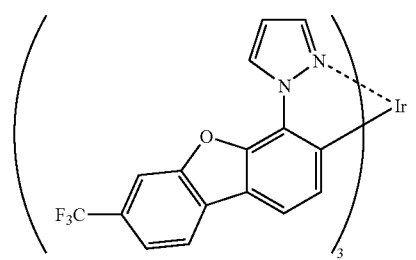
14-12 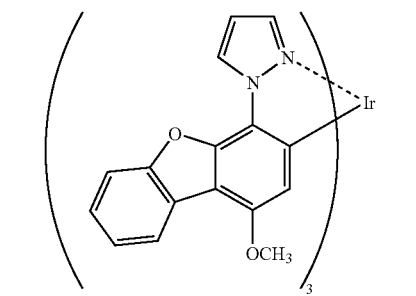
14-13 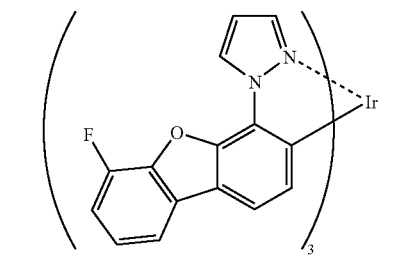
14-14 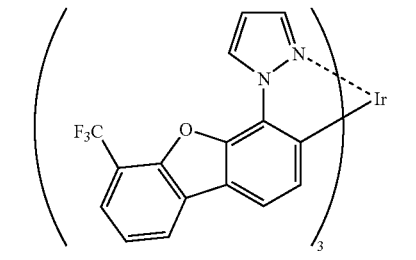
14-15 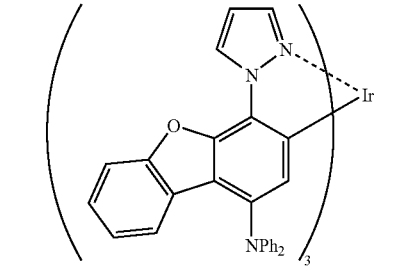
15-1 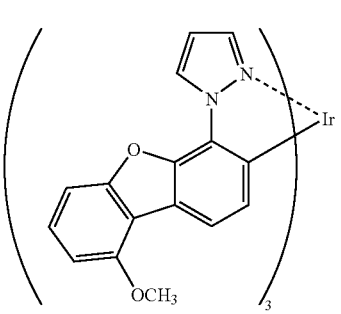
15-2 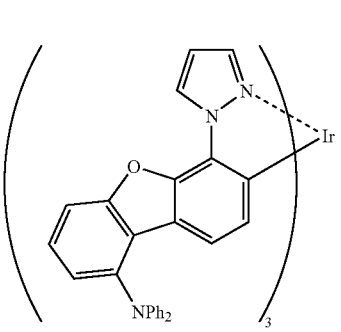
15-3 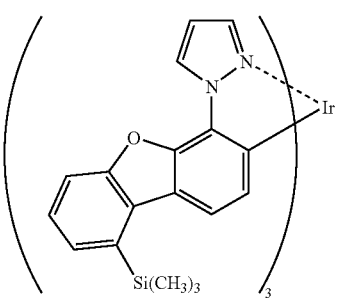
15-4 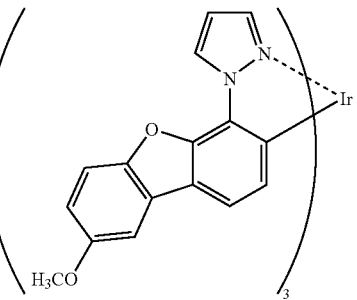
15-5 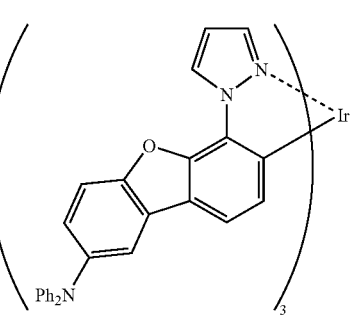

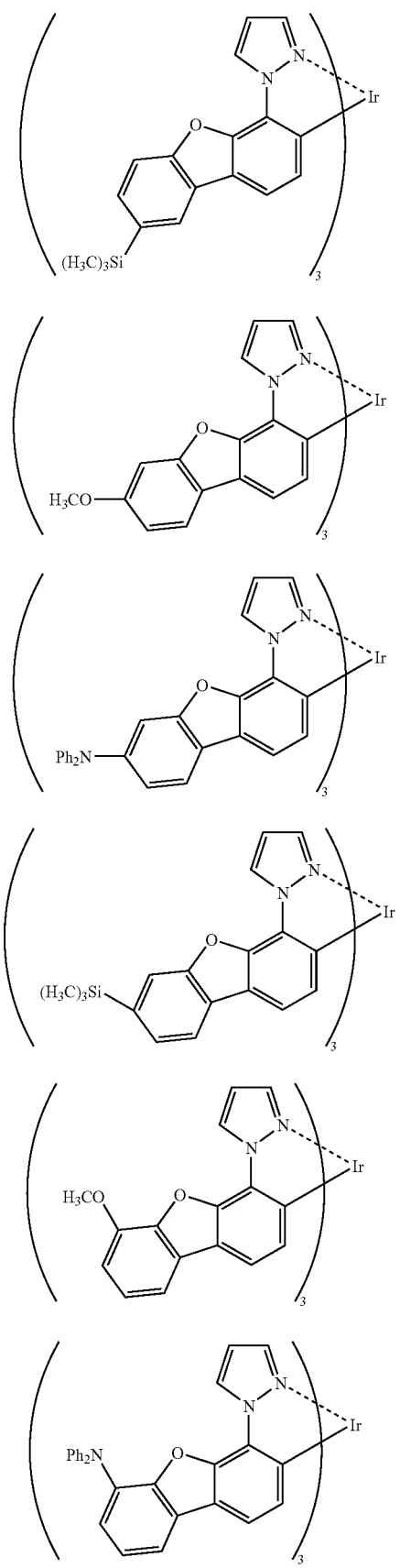

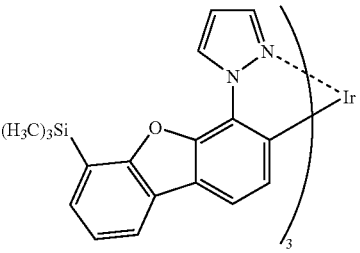

Organic Electroluminescent Device

The organic electroluminescent device in the invention will be described in detail below.

The organic electroluminescent device in the invention is an organic electroluminescent device comprising a pair of electrodes and at least one organic layer including a light-emitting layer between the pair of electrodes, and at least one organic layer contains the compound represented by formula (1). The compound represented by formula (1) is preferably a compound represented by formula (4), more preferably a compound represented by formula (5), and still more preferably a compound represented by formula (8).

It is preferred for the organic electroluminescent device of the invention to contain a phosphorescent material (an iridium complex, a platinum complex, a rhenium complex, an osmium complex, and a ruthenium complex are exemplified). As the phosphorescent material, a metal complex having a bidentate or higher polydentate ligand is preferred, and an iridium complex having a bidentate ligand is especially preferred.

As phosphorescent materials, the compounds (phosphorescent materials, metal complexes (platinum complexes)) disclosed, e.g., in Japanese Patent Application Nos. 2004-088575, 2004-162849 (JP-A-2005-310733), 2005-069963 (JP-A-2005-317516), 2004-271064, 2005-041939, 2004-279153 (JP-A-2006-093542), 2005-075769, 2005-075341, 2005-070992, and 2005-075340 are exemplified.

In the invention, the layers for containing the compound represented by formula (1), (4), (5) or (8) are not especially restricted, but it is preferred for the compound to be contained in a hole injecting layer, a hole transporting layer, an electron blocking layer, a light-emitting layer, a hole blocking layer, an exciton blocking layer, an electron transporting layer, or an electron injecting layer, more preferably the compound is contained in a hole transporting layer, a light-emitting layer, a hole injecting layer or an exciton blocking layer, and especially preferably contained in a light-emitting layer.

In the invention, the compound represented by formula (1), (4), (5) or (8) may be used as a host material or a light-emitting material in a light-emitting layer, but is preferably used as a light-emitting material.

In the invention, when the compound represented by formula (1), (4), (5) or (8) is contained in a light-emitting layer, the content of the compound of the invention in the light-emitting layer (the proportion of the weight of the compound of the invention accounting for in the total weight of the light-emitting layer) is preferably from 1 to 35 mass %, more preferably from 3 to 25 mass %, and especially preferably from 5 to 15 mass %.

The luminescent device in the invention comprises a substrate having thereon a cathode and an anode, and organic layers (the organic layers may be organic layers comprising an organic compound alone, or may be organic layers containing an inorganic compound) including an organic light-emitting layer (hereinafter sometimes referred to as merely "a light-emitting layer") between the electrodes. From the properties of the luminescent device, it is preferred that at least one electrode of the cathode and anode is transparent.

As the embodiment of lamination of the organic layers in the invention, lamination is preferably in order of a hole transporting layer, a light-emitting layer, and an electron transporting layer from the anode side. Further, a charge blocking layer may be provided between a hole transporting layer and a light-emitting layer, or between a light-emitting layer and an electron transporting layer. A hole injecting layer may be provided between the anode and a hole transporting layer, and an electron injecting layer may be provided between the cathode and an electron transporting layer. Each layer may be divided into a plurality of secondary layers.

The constituents of the light-emitting material of the invention are described in detail below.

Substrate

The substrate for use in the invention is preferably a substrate that does not scatter or attenuate the light emitted from the organic layers. The specific examples of the materials of the substrate include inorganic materials, e.g., yttria stabilized zirconia (YSZ), glass, etc., and organic materials, such as polyester, e.g., polyethylene terephthalate, polybutylene phthalate, polyethylene naphthalate, etc., polystyrene, polycarbonate, polyether sulfone, polyallylate, polyimide, polycycloolefin, norbornene resin, poly(chlorotrifluoroethylene), etc.

When glass is used as a substrate, non-alkali glass is preferably used as the material for reducing elution of ions from the glass. Further, when soda lime glass is used, it is preferred to provide a barrier coat such as silica. In the case of organic materials, materials excellent in heat resistance, dimensional stability, solvent resistance, electrical insulating properties and processability are preferably used.

The shape, structure and size of a substrate are not especially restricted, and these can be arbitrarily selected in accordance with the intended use and purpose of the luminescent device. In general, a substrate is preferably in a plate-like shape. The structure of a substrate may be a single layer structure or may be a lamination structure, and may consist of a single member or may be formed of two or more members.

A substrate may be colorless and transparent, or may be colored and transparent, but from the point of not scattering or attenuating the light emitted from an organic light-emitting layer, a colorless and transparent substrate is preferably used.

A substrate can be provided with a moisture permeation preventing layer (a gas barrier layer) on the front surface or rear surface.

As the materials of the moisture permeation preventing layer (the gas barrier layer), inorganic materials such as silicon nitride and silicon oxide are preferably used. The moisture permeation preventing layer (the gas barrier layer) can be formed, for example, by a high frequency sputtering method.

When a thermoplastic substrate is used, if necessary, a hard coat layer and an undercoat layer may further be provided.

Anode

An anode is generally sufficient to have the function of the electrode to supply positive holes to an organic layer. The shape, structure and size of an anode are not especially restricted, and these can be arbitrarily selected from known materials of electrode in accordance with the intended use and purpose of the luminescent device. An anode is generally preferably provided as a transparent anode.

As the materials of anode, for example, metals, alloys, metal oxides, electrically conductive compounds, and mixtures of these materials are preferably exemplified. The specific examples of the materials of anode include electrically conductive metal oxides, e.g., tin oxide doped with antimony or fluorine (ATO, FTO), tin oxide, zinc oxide, indium oxide, indium tin oxide (ITO), indium zinc oxide (IZO), etc., metals, e.g., gold, silver, chromium, nickel, etc., mixtures or laminates of these metals with electrically conductive metal oxides, inorganic electrically conductive substances, e.g., copper iodide, copper sulfide, etc., organic electrically conductive materials, e.g., polyaniline, polythiophene, polypyrrole, etc., laminates of these materials with ITO, etc. Of these materials, electrically conductive metal oxides are preferred, and ITO is especially preferred in view of productivity, high conductivity, transparency and the like.

An anode can be formed on the substrate in accordance with various methods arbitrarily selected from, for example, wet methods, e.g., a printing method, a coating method, etc., physical methods, e.g., a vacuum deposition method, a sputtering method, an ion plating method, etc., and chemical methods, e.g., a CVD method, a plasma CVD method, etc., taking the suitability with the material to be used in the anode into consideration. For example, in the case of selecting ITO as the material of an anode, the anode can be formed according to a direct current or high frequency sputtering method, a vacuum deposition method, an ion plating method, etc.

In the organic electroluminescent device in the invention, the position of the anode to be formed is not especially restricted and can be formed anywhere. The position can be arbitrarily selected in accordance with the intended use and purpose of the luminescent device, but preferably provided on the substrate. In this case, the anode may be formed on the entire surface of one side of the substrate, or may be formed at a part.

As patterning in forming an anode, patterning may be performed by chemical etching such as by photo-lithography, may be carried out by physical etching by laser, may be performed by vacuum deposition or sputtering on a superposed mask, or a lift-off method and a printing method may be used.

The thickness of an anode can be optionally selected in accordance with the materials of the anode, so that cannot be regulated unconditionally, but the thickness is generally from 10 nm to 50 µm or so, and is preferably from 50 nm to 20 µm.

The value of resistance of an anode is preferably $10^3 \Omega/\square$ or less, and more preferably $10^2 \Omega/\square$ or less. In the case where an anode is transparent, the anode may be colorless and transparent, or colored and transparent. For the coupling out of emission from the transparent anode side, transmittance is preferably 60% or more, and more preferably 70% or more.

In connection with transparent anodes, description is found in Yutaka Sawada supervised, *Tomei Denkyoku-Maku no Shintenkai* (*New Development in Transparent Electrode Films*), CMC Publishing Co., Ltd. (1999), and the description therein can be referred to. In the case of using a plastic substrate low in heat resistance, a transparent anode film formed with ITO or IZO at a low temperature of 150° C. or less is preferred.

Cathode

A cathode is generally sufficient to have the function of the electrode to supply electrons to an organic layer. The form, structure and size of a cathode are not especially restricted, and these can be arbitrarily selected from known materials of electrode in accordance with the intended use and purpose of the luminescent device.

As the materials of cathode, for example, metals, alloys, metal oxides, electrically conductive compounds, and mixtures of these materials are exemplified. The specific examples of the materials of cathode include alkali metals (e.g., Li, Na, K, Cs, etc.), alkaline earth metals (e.g., Mg, Ca, etc.), gold, silver, lead, aluminum, sodium-potassium alloy, lithium-aluminum alloy, magnesium-silver alloy, indium, rare earth metals, e.g., ytterbium, etc. These materials may be used by one kind alone, but from the viewpoint of the compatibility of stability and an electron injecting property, two or more kinds of materials are preferably used in combination.

As the materials constituting a cathode, alkali metals and alkaline earth metals are preferred of these materials in the point of an electron injecting property, and materials mainly comprising aluminum are preferred for their excellent preservation stability.

The materials mainly comprising aluminum mean aluminum alone, alloys of aluminum with 0.01 to 10 mass % of alkali metal or alkaline earth metal, or mixtures of these (e.g., lithium-aluminum alloy, magnesium-aluminum alloy, etc.).

The materials of a cathode are disclosed in detail in JP-A-2-15595 and JP-A-5-121172, and the materials described in these patents can also be used in the invention.

A cathode can be formed by known methods with no particular restriction. For example, a cathode can be formed according to wet methods, e.g., a printing method, a coating method, etc., physical methods, e.g., a vacuum deposition method, a sputtering method, an ion plating method, etc., and chemical methods, e.g., a CVD method, a plasma CVD method, etc., taking the suitability with the material constituting the cathode into consideration. For example, in the case of selecting metals as the material of a cathode, the cathode can be formed with one or two or more kinds of materials at the same time or in order by a sputtering method, etc.

Patterning in forming a cathode may be performed by chemical etching such as a method by photo-lithography, may be carried out by physical etching such as a method by laser, may be performed by vacuum deposition or sputtering on a superposed mask, or a lift-off method and a printing method may be used.

The position of the cathode to be formed is not especially restricted and can be formed anywhere in the invention. The cathode may be formed on the entire surface of the organic layer, or may be formed at a part.

A dielectric layer comprising fluoride or oxide of alkali metal or alkaline earth metal may be inserted between the cathode and the organic layer in a thickness of from 0.1 to 5 nm. The dielectric layer can be regarded as one kind of an electron injecting layer. The dielectric layer can be formed, for example, according to a vacuum deposition method, a sputtering method, an ion plating method, etc.

The thickness of a cathode can be optionally selected in accordance with the materials of the cathode, so that cannot be regulated unconditionally, but the thickness is generally from 10 nm to 5 µm or so, and is preferably from 50 nm to 1 µm.

A cathode may be transparent or opaque. A transparent cathode can be formed by forming a thin film of the materials of the cathode in a thickness of from 1 to 10 nm, and further laminating transparent conductive materials such as ITO and IZO.

Organic Layer

Organic layers in the invention will be described below.

The organic electroluminescent device of the invention is an organic electroluminescent device comprising a pair of electrodes and at least one organic layer including a light-emitting layer between the pair of electrodes, and at least one layer contains the compound represented by formula (1).

As organic layers other than the light-emitting layer, as described above, a hole transporting layer, an electron transporting layer, a charge blocking layer, a hole injecting layer and an electron injecting layer are exemplified.

Formation of Organic Layers

In the organic electroluminescent device of the invention, each layer constituting the organic layers can be preferably formed by any of dry film-forming methods such as a vacuum deposition method, a sputtering method, etc., a transfer method, and a printing method.

Organic Light-Emitting Layer

The organic light-emitting layer is a layer having functions to receive, at the time of electric field application, positive holes from the anode, hole injecting layer or hole transporting layer, and electrons from the cathode, electron injecting layer or electron transporting layer, and offer the field of recombination of positive holes and electrons to emit light.

The light-emitting layer in the invention may consist of light-emitting materials alone, or may comprise a mixed layer of a host material and a light-emitting material. The light-emitting material may be a fluorescent material or may be a phosphorescent material. Dopant may be one or two or more kinds.

The light-emitting layer may comprise one layer, or may be two or more layers, and each layer may emit light in different luminescent color.

Here, the host material means a material other than the light-emitting material of the materials constituting the light-emitting layer, and having at least one function of a function of dispersing a light-emitting material and maintaining the dispersion in the light-emitting layer, a function of receiving positive holes from an anode and a hole transporting layer, a function of receiving electrons from a cathode and an electron transporting layer, a function of transporting at least one of positive holes and electrons, a function of offering the place of recombination of positive holes and electrons, a function of shifting the energy of exciton generated by recombination to the light-emitting material, and a function of transporting at least one of positive holes and electrons to the light-emitting material.

The host material is preferably a charge transporting material. The host material may be used by one kind alone, or two or more kinds may be used. For example, the constitution of the mixture of an electron transporting host material and a hole transporting host material is exemplified. Further, a material not having a charge transporting property and not emitting light may be contained in the light-emitting layer.

As the kinds of host materials, it is more preferred to select two kinds of materials from among a metal complex host material, an aromatic hydrocarbon host material and a nitrogen-containing organic host material. It is still more preferred to contain any material of a metal complex host material, an aromatic hydrocarbon host material and a nitrogen-containing organic host material. It is preferred for the host material to be contained in the light-emitting layer in the proportion of from 5 to 99.9 mass %, and more preferably in the proportion of from 30 to 95 mass %.

The metal complex host materials will be described below. Metal ions constituting metal complexes are not especially restricted, but divalent or trivalent metal ions are preferred, a trivalent aluminum ion, a divalent zinc ion, a trivalent gallium ion, a divalent beryllium ion, and a divalent magnesium ion are more preferred, a trivalent aluminum ion, a trivalent gallium ion, and a divalent zinc ion are still more preferred, and a trivalent aluminum ion is especially preferred.

The aromatic hydrocarbon host materials will be described below. The aromatic hydrocarbon host materials are organic materials consisting of carbon and hydrogen alone. It is preferred for the aromatic hydrocarbon host materials not to have a condensed ring structure such as a naphthalene ring.

The nitrogen-containing organic host materials will be described below. The nitrogen-containing organic materials are organic materials having a nitrogen atom, for example, aniline derivatives, nitrogen-containing heterocyclic compounds and metal complexes having these compounds as the ligands are exemplified as the nitrogen-containing organic materials. The preferred nitrogen-containing organic materials are nitrogen-containing heterocyclic compounds and metal complexes having these compounds as the ligands, and the more preferred materials are compounds having a 5-membered nitrogen-containing heterocyclic ring (e.g., a pyrrole ring, a pyrazole ring, an imidazole ring, and a triazole ring, preferably a pyrrole ring and an imidazole ring, and more preferably a pyrrole ring), and the still more preferred materials are compounds having a condensed ring structure comprising a 5-membered nitrogen-containing heterocyclic ring and six condensed rings (preferably an indole ring, a carbazole ring).

In the invention it is preferred to contain the nitrogen-containing organic material in a light-emitting layer as the host material.

The external quantum efficiency of the luminescent device of the invention is preferably 5% or more. As the numerical value of the external quantum efficiency, the maximum value of the external quantum efficiency at the time of driving the device at 20° C., or the value of the external quantum efficiency in the vicinity of 360 cd/m$^2$ at the time of driving the device at 20° C. can be used.

The inner quantum efficiency of the luminescent device of the invention is preferably 30% or more. The inner quantum efficiency of a device is computed by the expression: inner quantum efficiency=external quantum efficiency/coupling out efficiency of light. In ordinary organic EL device, coupling out efficiency of light is about 20%, but it is possible to make coupling out efficiency of light 20% or more by various contrivances such as the shape of a substrate, the shape of electrodes, the thickness of an organic layer, the thickness of an inorganic layer, the refractive index of organic layers, and the refractive index of an inorganic layer.

It is preferred that the luminescent device of the invention is a device having at least three layers of a hole transporting layer, a light-emitting layer and an electron transporting layer.

The ionization potential of the host material contained in a light-emitting layer of the invention is preferably from 5.7 to 6.3 eV, more preferably from 5.75 to 6.2 eV, and still more preferably from 5.8 to 6.0 eV.

The ionization potential of the host material can be measured, e.g., with an atmospheric photoelectron spectrometer (AC-2, manufactured by Riken Keiki Co., Ltd.).

The degree of electron transfer of the host material in the light-emitting layer is preferably $1 \times 10^{-6}$ cm$^2$/Vs or more and $1 \times 10^{-1}$ cm$^2$/Vs or less, more preferably $5 \times 10^{-6}$ cm$^2$/Vs or more and $1 \times 10^{-2}$ cm$^2$/Vs or less, still more preferably $1 \times 10^{-5}$ cm$^2$/Vs or more and $1 \times 10^{-2}$ cm$^2$/Vs or less, and especially preferably $5 \times 10^{-5}$ cm$^2$/Vs or more and $5 \times 10^{-3}$ cm$^2$/Vs or less.

The degree of hole transfer of the host material in the light-emitting layer is preferably $1 \times 10^{-6}$ cm$^2$/Vs or more and $1 \times 10^{-1}$ cm$^2$/Vs or less, more preferably $5 \times 10^{-6}$ cm$^2$/Vs or more and $1 \times 10^{-2}$ cm$^2$/Vs or less, still more preferably $1 \times 10^{-5}$ cm$^2$/Vs or more and $1 \times 10^{-2}$ cm$^2$/Vs or less, and especially preferably $5 \times 10^{-5}$ cm$^2$/Vs or more and $1 \times 10^{-2}$ cm$^2$/Vs or less.

The glass transition points of the host material, and the materials of the electron transporting layer and hole transporting contained in the light-emitting layer of the invention are preferably 90° C. or more and 400° C. or less, more preferably 100° C. or more and 380° C. or less, still more preferably 120° C. or more and 370° C. or less, and especially preferably 140° C. or more and 360° C. or less.

From the viewpoint of blue color purity, the maximum wavelength of emission of the organic electroluminescent device of the invention is preferably 430 nm or more and 470 nm or less, and more preferably 440 nm or more and 460 nM or less. Further, the luminescent device of the invention may have the maximum wavelength of emission in the region of 490 nm or higher, and may be a luminescent device of white emission.

From the viewpoint of blue color purity, x value of CIE chromaticity values of emission of the organic electroluminescent device of the invention is preferably 0.22 or less, and more preferably 0.20 or less.

From the viewpoint of blue color purity, y value of CIE chromaticity values of emission of the organic electroluminescent device of the invention is preferably 0.25 or less, more preferably 0.20 or less, and still more preferably 0.15 or less.

From the viewpoint of blue color purity, the half value width of emission spectrum of the organic electroluminescent device of the invention is preferably 100 mm or less, more preferably 90 nm or less, still more preferably 80 nm or less, and especially preferably 70 nm or less.

The $T_1$ level (the energy level in the state of minimum triplet excitation) of the phosphorescent material is preferably 60 Kcal/mol or more (251.4 KJ/mol or more) and 90 Kcal/mol or less (377.1 KJ/mol or less), more preferably 62 Kcal/mol or more (259.78 KJ/mol or more) and 85 Kcal/mol or less (356.15 KJ/mol or less), and still more preferably 65 Kcal/mol or more (272.35 KJ/mol or more) and 80 Kcal/mol or less (335.2 KJ/mol or less).

The $T_1$ level (the energy level in the state of minimum triplet excitation) of the host material in the light-emitting layer is preferably 60 Kcal/mol or more (251.4 KJ/mol or more) and 90 Kcal/mol or less (377.1 KJ/mol or less), more preferably 62 Kcal/mol or more (259.78 KJ/mol or more) and 85 Kcal/mol or less (356.15 KJ/mol or less), and still more preferably 65 Kcal/mol or more (272.35 KJ/mol or more) and 80 Kcal/mol or less (335.2 KJ/mol or less).

The $T_1$ level (the energy level in the state of minimum triplet excitation) of the layer contiguous to the light-emitting layer (the hole transporting layer, electron transporting layer, charge blocking layer, exciton blocking layer, etc.) is preferably 60 Kcal/mol or more (251.4 KJ/mol or more) and 90 Kcal/mol or less (377.1 KJ/mol or less), more preferably 62 Kcal/mol or more (259.78 KJ/mol or more) and 85 Kcal/mol or less (356.15 KJ/mol or less), and still more preferably 65 Kcal/mol or more (272.35 KJ/mol or more) and 80 Kcal/mol or less (335.2 KJ/mol or less).

The $T_1$ level (the energy level in the state of minimum triplet excitation) of various kinds of materials such as a phosphorescent material, a host material, etc., can be computed from the end of the short wavelength of phosphorescence spectrum at 77 K of the material film vacuum deposited on a quartz glass plate.

The examples of fluorescent materials that can be used in the invention include benzoxazole derivatives, benzimidazole derivatives, benzothiazole derivatives, styrylbenzene derivatives, polyphenyl derivatives, diphenylbutadiene derivatives, tetraphenylbutadiene derivatives, naphthalimide derivatives, coumarin derivatives, condensed aromatic compounds, perinone derivatives, oxadiazole derivatives, oxazine derivatives, aldazine derivatives, pyraridine derivatives, cyclopentadiene derivatives, bisstyrylanthracene derivatives, quinacridone derivatives, pyrrolopyridine derivatives, thiadiazolopyridine derivatives, cyclopentadiene derivatives, styrylamine derivatives, diketopyrrolopyrrole derivatives, aromatic dimethylidine compounds, various metal complexes represented by metal complexes of 8-quinolinol derivatives and metal complexes of pyrromethene derivatives, polymer compounds such as polythiophene, polyphenylene, polyphenylenevinylene, etc., and compounds such as organic silane derivatives.

The examples of phosphorescent materials that can be used in the invention include complexes containing a transition metal atom or a lanthanoid atom.

The transition metal atoms are not especially restricted, but preferably ruthenium, rhodium, palladium, tungsten, rhenium, osmium, iridium and platinum are exemplified, and rhenium, iridium and platinum are more preferred.

As lanthanoid atoms, lanthanum, cerium, praseodymium, neodymium, samarium, europium, gadolinium, terbium, dysprosium, holmium, erbium, thulium, ytterbium, and lutetium are exemplified. Of these lanthanoid atoms, neodymium, europium and gadolinium are preferred.

As the examples of ligands of complexes, the ligands described, for example, in G. Wilkinson et al., *Comprehensive Coordination Chemistry*, Pergamon Press (1987), H. Yersin, *Photochemistry and Photophysics of Coordination Compounds*, Springer-Verlag (1987), and Akio Yamamoto, *Yuki Kinzoku Kagaku-Kiso to Oyo-(Organic Metal Chemistry—Elements and Applications)*, Shokabo Publishing Co. (1982) are exemplified.

As the specific examples of ligands, halogen ligands (preferably a chlorine ligand), nitrogen-containing heterocyclic ligands (e.g., phenylpyridine, benzoquinoline, quinolinol, bipyridyl, phenanthroline, etc.), diketone ligands (e.g., acetylacetone, etc.), carboxylic acid ligands (e.g., acetic acid ligand, etc.), carbon monoxide ligands, isonitrile ligands, and cyano ligands are preferably exemplified, and more preferably nitrogen-containing heterocyclic ligands are exemplified. These complexes may have one transition metal atom in a compound, or may be what is called polynuclear complexes having two or more transition metal atoms. They may contain dissimilar metal atoms at the same time.

It is preferred for phosphorescent materials to be contained in the light-emitting layer in an amount of from 0.1 to 40 mass %, and more preferably from 0.5 to 20 mass %.

The thickness of the light-emitting layer is not especially limited, but is generally preferably from 1 to 500 nm, more preferably from 5 to 200 nm, and still more preferably from 10 to 100 nm.

Hole Injecting Layer and Hole Transporting Layer

The hole injecting layer and the hole transporting layer are layers having a function to receive positive holes from the anode or anode side and transport the positive holes to the cathode side. The hole injecting layer and the hole transporting layer are specifically preferably the layers containing carbazole derivatives, triazole derivatives, oxazole derivatives, oxadiazole derivatives, imidazole derivatives, polyarylalkane derivatives, pyrazoline derivatives, pyrazolone derivatives, phenylenediamine derivatives, arylamine derivatives, amino-substituted chalcone derivatives, styrylanthracene derivatives, fluorenone derivatives, hydrazone derivatives, stilbene derivatives, silazane derivatives, aromatic tertiary amine compounds, styrylamine compounds, aromatic dimethylidine compounds, porphyrin compounds, organic silane derivatives, carbon, and various kinds of metal complexes represented by Ir complex having phenylazole or phenylazine as the ligand.

The thickness of the hole injecting layer and the hole transporting layer is preferably 500 nm or less from the viewpoint of lowering driving voltage.

The thickness of the hole transporting layer is preferably from 1 to 500 mm, more preferably from 5 to 200 nm, and still more preferably from 10 to 100 nm. The thickness of the hole injecting layer is preferably from 0.1 to 200 nm, more preferably from 0.5 to 100 nm, and still more preferably from 1 to 100 nm.

The hole injecting layer and the hole transporting layer may be a single layer structure comprising one or two or more of the above materials, or may be a multilayer structure comprising a plurality of layers of the same or different compositions.

Electron Injecting Layer and Electron Transporting Layer

The electron injecting layer and the electron transporting layer are layers having a function to receive electrons from the cathode or the cathode side and transport the electrons to the anode side. The electron injecting layer and the electron transporting layer are specifically preferably layers containing triazole derivatives, oxazole derivatives, oxadiazole derivatives, imidazole derivatives, fluorenone derivatives, anthraquinodimethane derivatives, anthrone derivatives, diphenylquinone derivatives, thiopyran dioxide derivatives, carbodiimide derivatives, fluorenylidene-methane derivatives, distyrylpyrazine derivatives, aromatic ring tetracarboxylic acid anhydride such as naphthalene, perylene, etc., phthalocyanine derivatives, various metal complexes represented by metal complexes of 8-quinolinol derivatives, metal complexes having metalphthalocyanine, benzoxazole, or benzothiazole as the ligand, organic silane derivatives, and the like.

It is preferred for the organic electroluminescent device in the invention to contain a material of metal complex in the electron transporting layer. The metal ions to constitute metal complexes are not especially restricted, but divalent or trivalent metal ions are preferred, a trivalent aluminum ion, a divalent zinc ion, a trivalent gallium ion, a divalent beryllium ion, and a divalent magnesium ion are more preferred, a trivalent aluminum ion, a trivalent gallium ion, and a divalent zinc ion are still more preferred, and a trivalent aluminum ion is especially preferred.

The thickness of each of the electron injecting layer and the electron transporting layer is preferably 500 nm or less from the viewpoint of lowering driving voltage.

The thickness of the electron transporting layer is preferably from 1 to 500 nm, more preferably from 5 to 200 nm, and still more preferably from 10 to 100 nm. The thickness of the electron injecting layer is preferably from 0.1 to 200 nm, more preferably from 0.2 to 100 nm, and still more preferably from 0.5 to 50 nm.

The electron injecting layer and the electron transporting layer may be a single layer structure comprising one or two or more of the above materials, or may be a multilayer structure comprising a plurality of layers of the same or dissimilar compositions.

Hole Blocking Layer

The hole blocking layer is a layer having a function of preventing the positive holes transported from the anode side to the light-emitting layer from passing through to the cathode side. In the invention, a hole blocking layer can be provided as the organic layer contiguous to the light-emitting layer on the cathode side.

As the examples of the organic compounds constituting the hole blocking layer, aluminum complexes, e.g., BAlq (bis-(2-methyl-8-quinolinolate)-4-(phenyl-phenolate)aluminum), etc., triazole derivatives, phenanthroline derivatives, e.g., BCP (2,9-dimethyl-4,7-diphenyl-1,10-phenanthroline), etc., can be exemplified.

The thickness of the hole blocking layer is preferably from 1 to 500 nm, more preferably from 5 to 200 nm, and still more preferably from 10 to 100 nm.

The hole blocking layer may be a single layer structure comprising one or two or more of the above materials, or may be a multilayer structure comprising a plurality of layers of the same or dissimilar compositions.

Protective Layer

In the invention the organic EL device may be completely protected with a protective layer.

It is sufficient for the materials to be contained in the protective layer to have a function capable of restraining the substances accelerating deterioration of the device, e.g., water, oxygen, etc., from entering the device.

The specific examples of such materials include metals, e.g., In, Sn, Pb, Au, Cu, Ag, Al, Ti, Ni, etc., metal oxides, e.g., MgO, SiO, $SiO_2$, $Al_2O_3$, GeO, NiO, CaO, BaO, $Fe_2O_3$, $Y_2O_3$, $TiO_2$, etc., metal nitrides, e.g., $SiN_x$, $SiN_xO_y$, etc., metal fluorides, e.g., $MgF_2$, LiF, $AlF_3$, $CaF_2$, etc., polyethylene, polypropylene, polymethyl methacrylate, polyimide, polyurea, polytetrafluoroethylene, polychlorotrifluoro-ethylene, polydichlorodifluoroethylene, copolymers of chlorotrifluoroethylene with dichlorodifluoroethylene, copolymers obtained by copolymerization of monomer mixtures containing tetrafluoroethylene and at least one comonomer, fluorine-containing copolymers having a cyclic structure on the main chain of the copolymer, water absorptive substances having a water absorption rate of not lower than 1%, moisture proofing substances having a water absorption rate of not higher than 0.1%.

The forming method of the protective layer is not especially restricted and, for example, a vacuum deposition method, a sputtering method, a reactive sputtering method, an MBE (molecular beam epitaxy) method, a cluster ion beam method, an ion plating method, a plasma polymerization method (a high frequency excitation ion plating method), a plasma CVD method, a laser CVD method, a heat CVD method, a gas source CVD method, a coating method, a printing method, a transfer method, etc., can be applied to the invention, Sealing Container The organic electroluminescent device of the invention may be completely sealed in a sealing container.

Further, a water absorber or an inert liquid may be filled in the space between the sealing container and the luminescent device. The water absorber is not especially restricted and, for example, barium oxide, sodium oxide, potassium oxide, calcium oxide, sodium sulfate, calcium sulfate, magnesium sulfate, phosphorus pentoxide, calcium chloride, magnesium chloride, copper chloride, cesium fluoride, niobium fluoride, calcium bromide, vanadium bromide, molecular sieve, zeolite, magnesium oxide, etc., can be exemplified. The inert liquid is not particularly limited and, for example, paraffins, liquid paraffins, fluorine solvents, such as perfluoroalkane, perfluoroamine, perfluoroether, etc., chlorine solvents, and silicone oils are exemplified.

Driving Method

Emission can be obtained by the application of DC (if necessary, an alternating current factor may be contained) voltage (generally from 2 to 15 V) or direct electric current between the anode and cathode of the organic electroluminescent device of the invention.

In connection with the driving methods of the organic electroluminescent device of the invention, the driving methods disclosed in JP-A-2-148687, JP-A-6-301355, SP-A-5-29080, JP-A-7-134558, JP-A-8-234685, JP-A-8-241047, Japanese Patent 2784615, and U.S. Pat. Nos. 5,828,429 and 6,023,308 can be applied to the invention.

EXAMPLE

Synthesis of Bromodibenzofuran (Compound 16-1)

Under nitrogen current at −78° C., an n-butyl lithium hexane solution (1.6M, 69 ml) is dropped to a THF solution (175 ml) containing 16.82 g of dibenzofuran, and the temperature of the mixture is raised to room temperature over 80 minutes. The obtained solution is again cooled to −78° C., 19.0 ml of 1,2-dibromoethane is added to the solution, and the temperature of the solution is raised to room temperature over 120 minutes. Water is added to the obtained reaction solution to stop the reaction. Organic layers extracted from the obtained mixture with ethyl acetate are dried with sodium sulfate, and then concentrated with an evaporator to obtain 12.35 g of Compound 16-1.

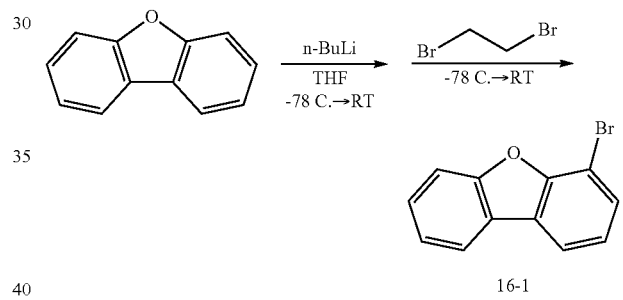

16-1

Synthesis of Pyrazolyldibenzofuran (Compound 17-1)

Under nitrogen current, a mixture containing 12.35 g (50 mmol) of bromodibenzofuran (Compound 16-1), 5.11 g (75 mmol) of pyrazole, 358 mg (2.5 mmol) of cuprous oxide (I), 1.37 g (10 mmol) of salicylaldoxime, 32.6 g (100 mmol) of cesium carbonate, and 100 ml of DMF is reacted under reflux with heating for 6 hours. DMF is distilled off from the resulting mixture by heating under reduced pressure. Ethyl acetate is added to the residue and the mixture is filtered with Celite, and a 1M sodium hydroxide aqueous solution is added to the obtained liquid. Organic layers extracted from the obtained mixture with ethyl acetate are dried with sodium sulfate. The organic layers are concentrated and refined by silica gel column chromatography to obtain 9.12 g (39 mmol) of Compound 17-1.

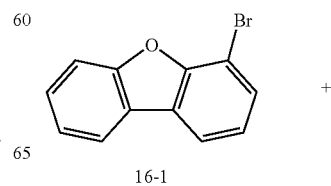

16-1

+

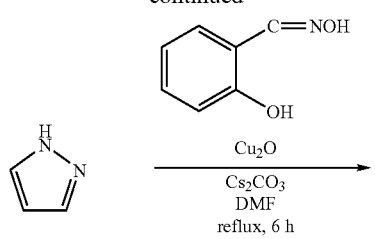

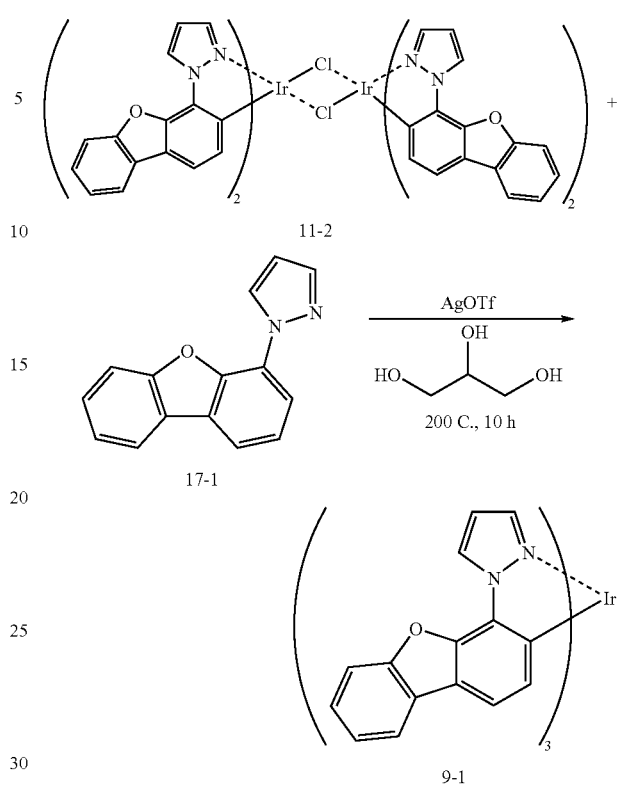

Synthesis of Compound 11-2

Under nitrogen current, a mixture containing 2.58 g (11 mmol) of pyrazolyldibenzofuran (Compound 17-1), 2.61 g (5 mmol) of potassium chloroiridate, 30 ml of water, and 50 ml of 2-methoxyethanol is reacted under reflux with heating for 3 hours. The obtained suspension is filtered to obtain 3.73 g of Compound 11-2 as yellow powder.

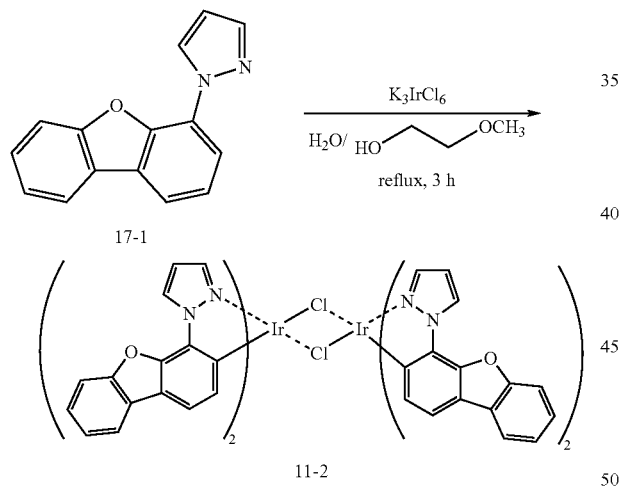

Synthesis of Compound 9-1

Under nitrogen current, a mixture containing 1.64 g (1.18 mmol) of Compound 11-2, 0.892 g (3.54 mmol) of pyrazolyldibenzofuran (Compound 17-1), 0.910 g (3.54 mmol) of silver trifluoromethanesulfonate, and 30 ml of glycerol is reacted at 200° C. for 10 hours. After cooling the reaction solution, methanol is added thereto, and the obtained suspension is filtered. The obtained powder is refined by silica gel column chromatography to obtain 1.28 g (1.44 mmol, 61%) of Compound 9-1.

$^1$H NMR (300 MHz, CDCl$_3$): δ 6.60 (dd, 3H), 7.37-7.56 (m, 9H), 7.66 (d, 3H), 7.78-7.92 (m, 6H), 8.00 (dd, 3H), 8.09 (dd, 3H), 8.66 (d, 3H)

The emission spectrum of Compound 9-1 of the invention is measured. The measurement is performed in EPA (a mixed solution comprising ethyl ether, isopentane, and ethyl alcohol in a proportion of 5/5/2) at room temperature. The result obtained is shown in Table 1 below with the maximum emission wavelengths of well-known compounds Ir(3 bppz)$_3$, Ir(2dmflpz)$_3$ and Ir(4 bppz)$_3$ shown below disclosed in Patent Document 3 (WO 2004/085,450).

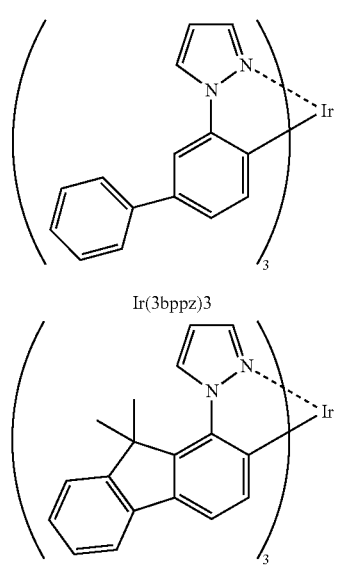

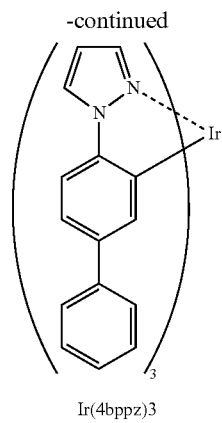

Ir(4bppz)3

TABLE 1

Maximum Emission Wavelength of Metal Complex under Room Temperature

| Metal Complex | Maximum Emission Wavelength (nm) |
| --- | --- |
| Ir(3bppz)$_3$ | 466* |
| Ir(2dmflpz)$_3$ | 478* |
| Ir(4bppz)$_3$ | 420* |
| Compound 9-1 | 454 |

*The emission data of the compounds disclosed in WO 04/085450 are those measured in 2-MeTHF.

It can be seen from the above emission wavelengths that Ir(4 bppz)$_3$ and Compound 9-1 emit blue light in good color purity,

Example 1

An ITO thin film is sputtered on the cleaned surface of a quartz glass substrate as anode, and the substrate is placed in a vacuum evaporator, copper phthalocyanine is deposited on the substrate in a thickness of 10 nm, and NPD (N,N'-di-α-naphthyl-N,N'-diphenyl)benzidine is deposited thereon in a thickness of 40 mm. Iridium complex (Compound 9-1) as a light-emitting material and mCP (1,3-di(9H-carbazol-9-yl) benzene as a host material in a ratio of 10/90 (by mass) are deposited on the above deposited film in a thickness of 20 nm, then BAlq is deposited thereon in a thickness of 6 nm, and then Alq (tris(8-hydroxyquinoline)aluminum complex) is deposited on the above film in a thickness of 20 nm. Lithium fluoride is deposited thereon in a thickness of 3 nm, followed by deposition of aluminum in a thickness of 60 nm to prepare a device. The obtained EL device is subjected to application of DC constant voltage with a source measure unit Model 2400 (manufactured by Toyo Technica Co., Ltd.) to emit light. It is confirmed that the emission of phosphorescence originating in the iridium complex (Compound 9-1) is obtained.

Devices are manufactured in the same manner as in Example 1. Emission originating in each light-emitting material is obtained in each device. The constitutions of manufactured devices are shown in Table 2 below.

TABLE 2

Light-Emitting Materials of Manufactured Devices

| Manufactured Device | Light-Emitting Material | Host Material |
| --- | --- | --- |
| Comparative Example 1 | Ir(3bppz)$_3$ | mCP |
| Comparative Example 2 | Ir(2dmflpz)$_3$ | mCP |
| Comparative Example 3 | Ir(4bppz)$_3$ | mCP |
| Example 1 | Compound 9-1 | mCP |
| Example 2 | Compound 9-1 | Compound 21-1 |

21-1

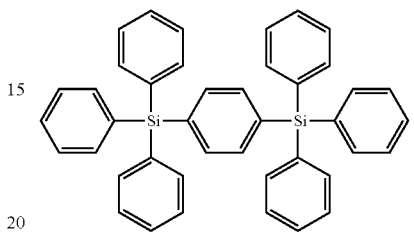

The results of Examples 1 to 2 and Comparative Examples 1 to 3 are shown together in Table 3 below. Each value is shown in a relative value with the value in Example 1 being a standard. The duration of life of device is the time until the half life time of luminance is reached by constant current driving at initial luminance of 360 ca/m$^2$. The luminous efficacy and driving voltage are respectively computed from the value of the time of driving at initial luminance of 360 ca/m$^2$.

TABLE 3

Results of Comparison of Example 1 and Comparative Examples (in a relative value)

| Example No. | Luminous Efficacy | Driving Voltage | Duration of Life of Device |
| --- | --- | --- | --- |
| Example 1 | 1 | 1 | 1 |
| Example 2 | 0.9 | 1.2 | 0.9 |
| Comparative Example 1 | 0.5 | 1.8 | 0.5 |
| Comparative Example 2 | 0.7 | 1.2 | 0.7 |
| Comparative Example 3 | 0.1 | 2.0 | 0.2 |

From the comparison of Examples 1 and 2 with Comparative Examples 1 to 3, it is seen that organic electroluminescent devices using the compound of the invention show good luminous efficacy, low driving voltage, and long duration of life of device, so that the devices of the invention are excellent in every performance.

Further, from the comparison of Examples 1 and 2, it is confirmed that particularly the organic electroluminescent device using a nitrogen-containing organic material as the host material shows better luminous efficacy, lower driving voltage, and longer duration of life of device, so that excellent in every performance.

The compound according to the invention emits blue light having good color purity. Further, according to the device using the compound of the invention, improvement in all performances of luminous efficacy, driving voltage and duration of life of device has been achieved.

The compounds represented by formula (1), (4), (5) or (8) emit blue light in high luminous efficacy and good color purity. In an organic electroluminescent device using these compounds as light-emitting materials, blue emission can be obtained in high color purity and high efficiency, and further, driving voltage can be held down low and long duration of life can be achieved.

The entire disclosure of each and every foreign patent application from which the benefit of foreign priority has been claimed in the present application is incorporated herein by reference, as if fully set forth.

What is claimed is:

1. An organic electroluminescent device comprising:
a pair of electrodes; and
an organic layer between the pair of electrodes, which comprises a light-emitting layer and contains a compound represented by the following formula (8):

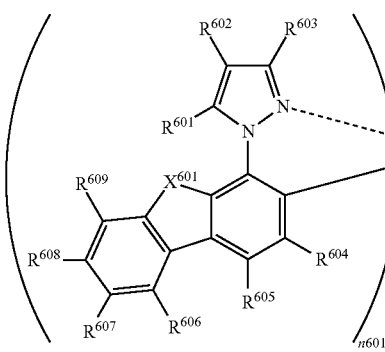

Formula (8)

wherein
the valence of Ir is trivalent;
$L^{601}$ represents a ligand;
$n^{601}$ represents an integer of 3;
$m^{601}$ represents an integer of 0;
$X^{601}$ represents an oxygen atom or a sulfur atom;
$R^{601}, R^{602}, R^{603}, R^{604}, R^{605}, R^{606}, R^{607}, R^{608}$ and $R^{609}$ each represent a hydrogen atom or a substituent; and
the dashed line represents a coordinate bond.

2. The organic electroluminescent device of claim 1, wherein the compound represented by the formula (8) is contained in the light-emitting layer.

3. The organic electroluminescent device of claim 1, wherein the light-emitting layer contains a nitrogen-containing organic material as a host material.

4. The organic electroluminescent device of claim 1, wherein the organic layer further comprises an electron-transporting layer containing a metal complex material.

5. A compound represented by the following formula (8):

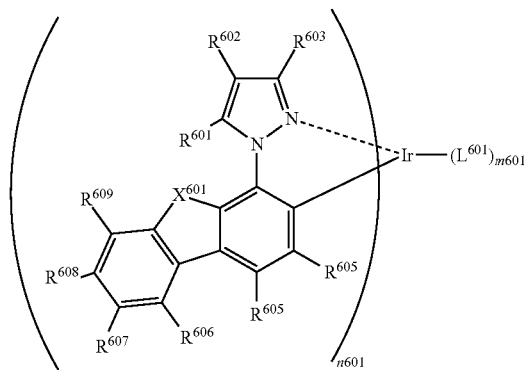

Formula (8)

wherein
the valence of Ir is trivalent;
$L^{601}$ represents a ligand;
$n^{601}$ represents an integer of 3;
$m^{601}$ represents an integer of 0;
$X^{601}$ represents an oxygen atom or a sulfur atom;
$R^{601}, R^{602}, R^{603}, R^{604}, R^{605}, R^{606}, R^{607}, R^{608}$ and $R^{609}$ each represents a hydrogen atom or a substituent; and
the dashed line represents a coordinate bond.

6. The organic electroluminescent device of claim 1, wherein $X^{601}$ represents an oxygen atom.

7. The compound of claim 5, wherein $X^{601}$ represents an oxygen atom.

* * * * *